US008784862B2

(12) United States Patent
Horres et al.

(10) Patent No.: US 8,784,862 B2
(45) Date of Patent: *Jul. 22, 2014

(54) COMPOUNDS AND METHOD FOR COATING SURFACES IN A HEMOCOMPATIBLE MANNER

(75) Inventors: Roland Horres, Stolberg (DE); Marita Katharina Linssen, Göttingen (DE); Michael Hoffmann, Eschweiler (DE); Erika Hoffmann, Eschweiler (DE); Donate DiBiase, Aachen (DE); Volker Faust, Aachen (DE)

(73) Assignee: Hemoteq AG, Würselen (DE)

( * ) Notice: Subject to any disclaimer, the term of this patent is extended or adjusted under 35 U.S.C. 154(b) by 247 days.

This patent is subject to a terminal disclaimer.

(21) Appl. No.: 12/827,710

(22) Filed: Jun. 30, 2010

(65) Prior Publication Data
US 2011/0009955 A1 Jan. 13, 2011

Related U.S. Application Data

(62) Division of application No. 10/513,982, filed as application No. PCT/DE03/01253 on Apr. 15, 2003.

(60) Provisional application No. 60/378,676, filed on May 9, 2002.

(30) Foreign Application Priority Data

May 10, 2002 (DE) .................................. 102 21 055

(51) Int. Cl.
| | | |
|---|---|---|
| *A61F 2/82* | (2013.01) | |
| *A61K 31/337* | (2006.01) | |
| *A61K 31/436* | (2006.01) | |
| *A61K 9/00* | (2006.01) | |
| *A61P 29/00* | (2006.01) | |
| *A61L 31/10* | (2006.01) | |
| *C08L 5/10* | (2006.01) | |
| *A61L 33/08* | (2006.01) | |
| *A61L 31/16* | (2006.01) | |
| *A61K 31/722* | (2006.01) | |
| *A61K 31/727* | (2006.01) | |
| *A61K 31/095* | (2006.01) | |
| *A61K 31/045* | (2006.01) | |
| *A61K 31/075* | (2006.01) | |
| *A61K 31/11* | (2006.01) | |
| *A61K 31/12* | (2006.01) | |
| *A61K 31/28* | (2006.01) | |
| *A61K 31/33* | (2006.01) | |
| *A61K 31/21* | (2006.01) | |
| *A61K 31/13* | (2006.01) | |

(52) U.S. Cl.
CPC . *A61L 31/10* (2013.01); *C08L 5/10* (2013.01); *A61L 33/08* (2013.01); *A61L 31/16* (2013.01); *A61K 31/722* (2013.01); *A61K 31/727* (2013.01); *A61K 31/095* (2013.01); *A61K 31/045* (2013.01); *A61K 31/075* (2013.01); *A61K 31/11* (2013.01); *A61K 31/12* (2013.01); *A61K 31/28* (2013.01); *A61K 31/33* (2013.01); *A61K 31/21* (2013.01); *A61K 31/13* (2013.01)
USPC ............ 424/423; 514/1.1; 514/579; 514/675; 514/693; 514/706; 514/715; 514/724; 514/740; 427/2.25; 623/1.43; 623/1.46

(58) Field of Classification Search
CPC ........... C08L 5/10; A61L 31/10; A61L 33/08; A61L 31/16; A61K 31/722; A61K 31/727; A61K 31/095; A61K 31/045; A61K 31/075; A61K 31/11; A61K 31/12; A61K 31/28; A61K 31/33; A61K 31/21; A61K 31/13; A61K 31/16; A61K 31/185
USPC ................ 424/423; 623/1.43, 1.46; 427/2.25; 514/1.1, 579, 675, 693, 706, 715, 724, 514/740
See application file for complete search history.

(56) References Cited

U.S. PATENT DOCUMENTS

| | | | | |
|---|---|---|---|---|
| 5,206,318 A | * | 4/1993 | Kobayashi et al. | ...... 526/238.23 |
| 5,583,121 A | | 12/1996 | Chaudry et al. | |

(Continued)

FOREIGN PATENT DOCUMENTS

| | | |
|---|---|---|
| CA | 2363119 | 4/2007 |
| DE | 19724869 C2 | 5/1999 |

(Continued)

OTHER PUBLICATIONS

Vann et al. (Eur. J. Biochem., 116, 359-364, Published 1981).*

(Continued)

*Primary Examiner* — Richard Schnizer
*Assistant Examiner* — Alma Pipic
(74) *Attorney, Agent, or Firm* — Meyertons, Hood, Kivlin, Kowert & Goetzel, P.C.; Eric B. Meyertons

(57) ABSTRACT

The invention concerns oligosaccharides and polysaccharides as well as the use of these oligosaccharides and/or polysaccharides, which contain the sugar unit N-acylglucosamine or N-acylgalactosamine for the production of hemocompatible surfaces as well as methods for the hemocompatible coating of surfaces with said oligosaccharides and/or polysaccharides, which imitate the common biosynthetic precursor substance of heparin, heparan sulphates and chitosan. The invention further describes methods for producing said oligosaccharides and/or polysaccharides and discloses various possibilities of using hemocompatibly coated surfaces. The invention relates particularly to the use of said oligosaccharides and/or polysaccharides on stents with at least one according to invention deposited hemocompatible coating, which contains an antiproliferative, antiinflammatory and/or antithrombotic active agent, methods for the preparation of said stents as well as the use of said stents for the prevention of restenosis.

13 Claims, 13 Drawing Sheets

(56) References Cited

U.S. PATENT DOCUMENTS

| | | | |
|---|---|---|---|
| 5,718,862 A | | 2/1998 | Thompson |
| 6,140,481 A | | 10/2000 | Hara et al. |
| 6,179,817 B1 | * | 1/2001 | Zhong ................ 604/265 |
| 6,238,795 B1 | | 5/2001 | Strom et al. |
| 6,299,604 B1 | | 10/2001 | Ragheb et al. |
| 6,489,311 B1 | | 12/2002 | Kennedy |
| 7,314,860 B2 | | 1/2008 | Lassila et al. |
| 7,884,087 B1 | | 2/2011 | Bellini et al. |
| 2001/0000802 A1 | * | 5/2001 | Soykan et al. ............ 623/1.13 |
| 2003/0059454 A1 | * | 3/2003 | Barry et al. .............. 424/423 |
| 2005/0176678 A1 | | 8/2005 | Horres et al. |

FOREIGN PATENT DOCUMENTS

| | | |
|---|---|---|
| JP | S56-161803 | 12/1981 |
| WO | 8605789 | 10/1986 |
| WO | 9927976 A1 | 6/1999 |

OTHER PUBLICATIONS

Nelson et al. (Cardiovasc. Intervent. Radiol., 23, 252-255).*
Kroncke et al. (Journal of Bacteriology, vol. 172, No. 2, Published Feb. 1990, pp. 1085-1091).*
Hoffmann et al. (Materialwissenschaft und Werkstofftechnik, vol. 32, Issue 2, Published online Feb. 5, 2001, pp. 110-115).*
Copending U.S. Appl. No. 10/483,545 Remarks Jul. 11, 2011.*
Copending U.S. Appl. No. 10/483,545 Claims Jul. 11, 2011.*
Baumann et al. (Biomedical Polymers and Polymer Therapeutics, pp. 177-193, Published 2001).*
Modis (CRC Organization of the Extracellular Matrix: A polarization Microscopic Approach, p. 159, Published 1991).*
MSDS for Heparin Disaccharide sodium salt (Sigma-Aldrich, accessed May 17, 2013).*
D. F. Williams, Definitions in Biomaterials: Proceedings of a Consensus Conference of the European Society for Biomaterials, Chester, England, Mar. 3-5, 1986, pp. 24, 25, 63, 68, and 69, 1st ed. Elsevier Publishing Company, 1987.*
Hricovini et al., "Motional Properties of *E. coli* Polysaccharide K5 in Aqueous Solution Analyzed by NMR Relaxation Measurements", Carbohydrate Research, 1997, 300, 69-76.
Muzzarelli et al., "N-(Carboxymethylidene)chitosans and N-(Carboxymethyl)chitosans: Novel Chelating Polyampholytes Obtained from Chitosan Glyoxylate" Carbohydrate Research 1982, 107, 199-214.
Nemtsev et al., "Deacetylation of Chitin Under Homogenous Conditions" 2002, Prikladnaa biohimia i mikrobiologia 38:6, 609-615. (Abstract).
Vann et al. "The Structure of the Capsular Polysaccharide (K5 Antigen) of Urinary-Tract-Infective *Escherichia coli* 010:K5:H4" 1981, Eur. J. Biochem. 116, 359-364.
Finke et al., "Biosynthesis of the *Escherichia coli* K5 Polysaccharide, a Representative of Group II Capsular Polysaccharides: Polymerization In Vitro and Characterization of the Product" Journal of Bacteriology 1991, 173, 4088-4094.
Baumann et al. "Concepts for Improved Regioselective Placement of O—sulfo, N—sulfo, N—acetyl, N—carboxymethyl Groups in Chitosan Derivatives" Carbohydrate Research 2001, 331, 43-57.
Legoux et al. "N-Acetyl-Heparosan Lyase of *Escherichia coli* W: Gene Cloning and Expression", J. Bacteriology 1996, 178, 7260-7264.
Gupta et al. "Enzymatic Degradation of the Capsular K5-Antigen of *E. coli* by Coliphage K5" FEMS Microbiology Letters vol. 16, 13-17, 1983.
Search Report from PCT Application No. PCT/DE2003/01253.
International Preliminary Examination Report from PCT Application No. PCT/DE2003/01253.
Office Action issued Sep. 25, 2008 for U.S. Appl. No. 10/513,982.
Office Action issued Dec. 23, 2009 for U.S. Appl. No. 10/513,982.
Office Action issued May 12, 2011 for U.S. Appl. No. 10/513,982.
Final Office Action issued Mar. 12, 2009 for U.S. Appl. No. 10/513,982.
Final Office Action issued Oct. 14, 2010 for U.S. Appl. No. 10/513,982.

* cited by examiner

3a

3b

3c a.) Ac-heparin stent b.) uncoated stent

After 1 week

After 4 weeks

After 6 weeks

After 12 weeks

COMPOUNDS AND METHOD FOR COATING SURFACES IN A HEMOCOMPATIBLE MANNER

PRIORITY CLAIM

This application is a Divisional of U.S. patent application Ser. No. 10/513,982 entitled "Compounds and method for coating surfaces in a hemocompatible manner" filed on Nov. 8, 2004, which is a National Stage Entry of International Application No. PCT/DE03/01253 filed Apr. 15, 2003, which claims the benefit of German Patent Application No. DE 102 21 055.1 filed May 10, 2002 and U.S. Provisional Patent Application No. 60/378,676, filed May 9, 2002.

BACKGROUND OF THE INVENTION

1. Field of the Invention

The invention relates to the use of oligo- and/or polysaccharides containing the sugar building block N-acylglucosamine and/or N-acylgalactosamine for the preparation of hemocompatible surfaces, methods for the hemocompatible coating of surfaces with said oligo- and/or polysaccharides as well as the use of the hemocompatibly coated surfaces.

2. Description of the Relevant Art

In the human body the blood gets in contact with surfaces other than the internal face of natural blood vessels only in case of an injury. Consequently the blood coagulation system is always activated to reduce the bleeding and to prevent a life-threatening loss of blood if blood gets in contact with foreign surfaces. Due to the fact that an implant also represents a foreign surface all patients receiving an implant which is permanently in contact with blood are treated for the duration of the blood contact with drugs, with so called anticoagulants which suppress the blood coagulation. This is also true for patients applicated an extracorporeal circulation such as hemodialysis patients. However this coagulation suppressive medication is in some extent afflicted with considerable side effects which range from loss of hair, nausea and vomitus beyond thrombocytopenia, hemorrhagic skin necroses and increased hemorrhagic diathesis up to side effects with a fatal outcome such as cerebral hemorrhages.

Thus there is a demand for non-thrombogenic, hemocompatible materials such as protheses, organ spareparts, membranes, cannulae, tubes, blood containers, stents etc. which do not activate the coagulation system in case of blood contact and do not cause coagulation of the blood.

EP-B-0 333 730 describes a method for preparation of hemocompatible substrates by incorporation, adhesion and/or modification and attachment of non-thrombogenic endothelial cell surface polysaccharide (HS-I). The immobilization of this specific endothelial cell surface proteoheparan sulphate HS I on biological or artificial surfaces causes that suchlike coated surfaces become blood compatible and suitable for the permanent blood contact. However, it is disadvantageous that said process for the generation of HS I requires the cultivation of endothelial cells, so that the economical usability of said process is very limited because the cultivation of endothelial cells is time consuming, and relatively large amounts of cultivated endothelial cells are only available at a considerably high cost.

SUMMARY OF THE INVENTION

It is the object of the present invention to provide substances for the hemocompatible coating of surfaces as well as methods for hemocompatible coating of surfaces and their use on surfaces for the prevention or reduction of undesired reactions.

Particularly it is the object of the present invention to provide medical products, which allow a continuous controlled ingrowth of the medical product—on the one hand by suppression of the cellular reactions during the first days and weeks after the implantation by means of the chosen active agents and active agent combinations and on the other hand by providing an atrombogeneous resp. inert resp. biocompatible surface, which guarantees, that with decreasing of the active agent influence no reactions on the present alien surface occur anymore, which also can lead to complications on the long-term.

This object is solved by the technical teaching of the independent claims of the present invention. Further advantageous embodiments of the invention are evident from the dependent claims, the description, the figures and the examples.

BRIEF DESCRIPTION OF THE DRAWINGS

Advantages of the present invention will become apparent to those skilled in the art with the benefit of the following detailed description of embodiments and upon reference to the accompanying drawings in which:

FIG. 3b shows an example of a compound according to the general formula Ib and FIG. 3c shows a section with a typical structure for a N-carboxymethylated, partially N-acetylated chitosan.

Thereby SH1 is a with heparin covalently coated stent, SH2 is a with chondroitinsulphate coated stent; SH3 is a stent coated with polysaccharides gained from the erythrocytic glycocalix and SH4 is a with Ac-heparin covalently coated stainless steel coronary stent.

Figure 5:
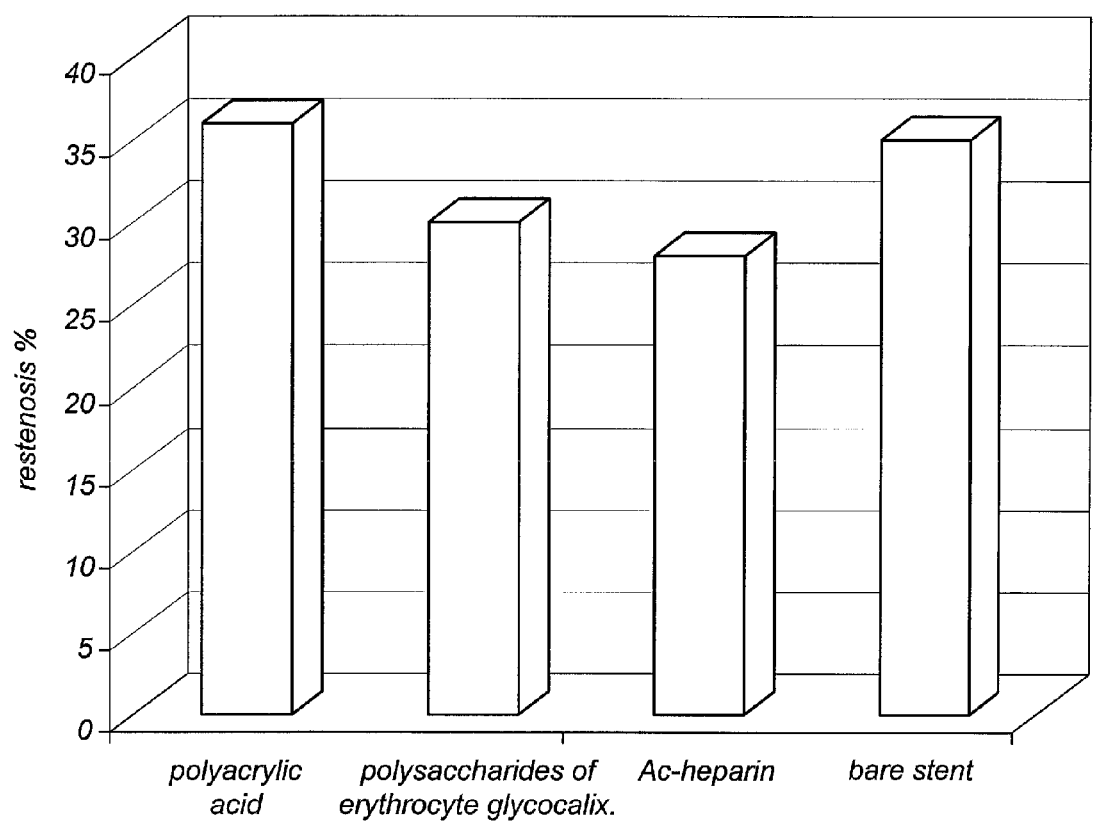

FIG. 5 shows a schematic presentation of the restenosis rate of with completely desulphated and N-reacetylated heparin (Ac-heparin) covalently coated stents and with oligo- and polysaccharides of the erythrocytic glycocalix coated stents in comparison to the uncoated stent and with polyacrylic acid (PAS) coated stents after 4 weeks of implantation time in pork.

Figure 6:
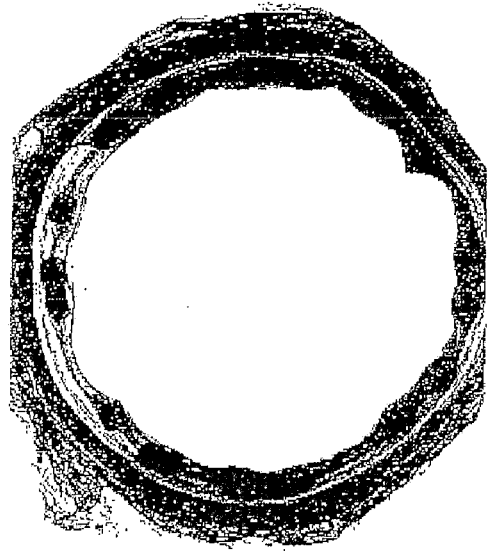
Figure 6:
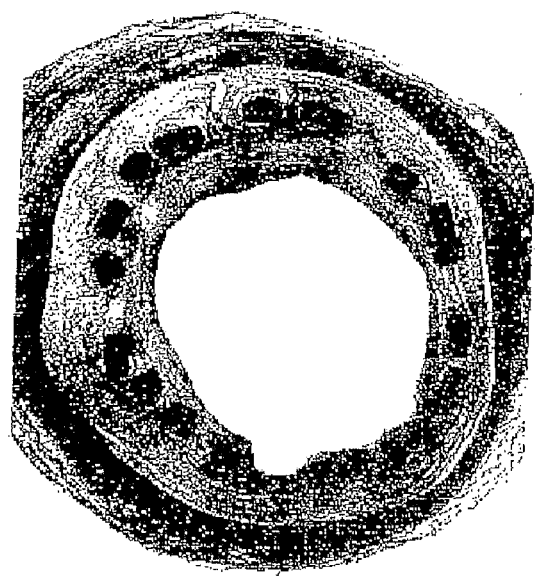

FIG. 6: Quantitative coronary angiography:

Images of the cross sections through the stent containing vessel-segment of one with Ac-heparin coated stent (a.) and as comparison of one uncoated (unco.) stent (b.). After four weeks in the animal experiment (pork) a clear difference in the thicknesses of the formed neointimas can be observed.

Figure 7:
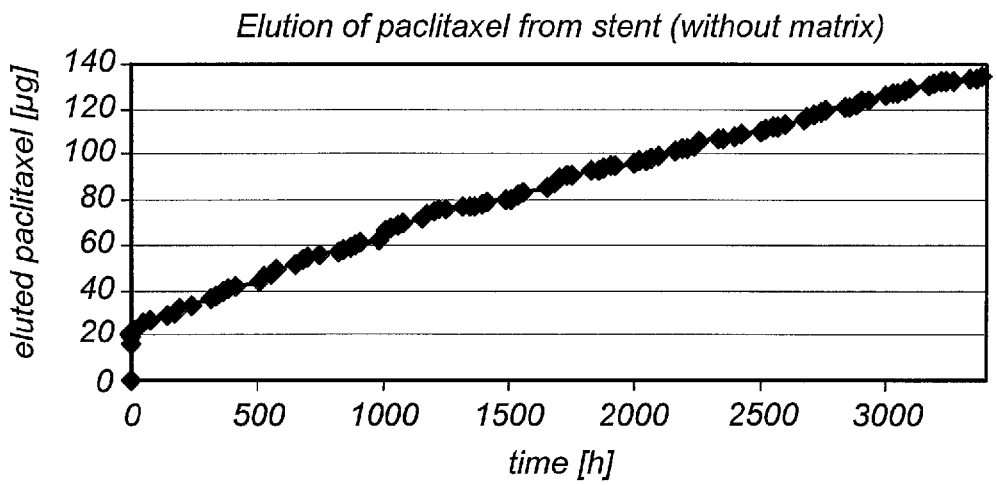

FIG. 7: Elution plot of paclitaxel from the stent (without support medium).

Figure 8:
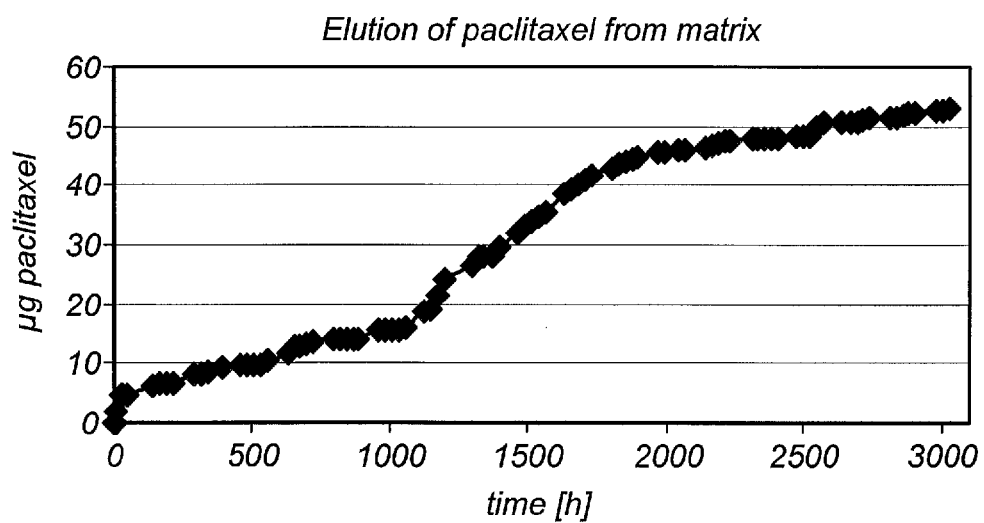

FIG. 8: Elution diagram of paclitaxel embedded into PLGA-matrix.

Figure 9:
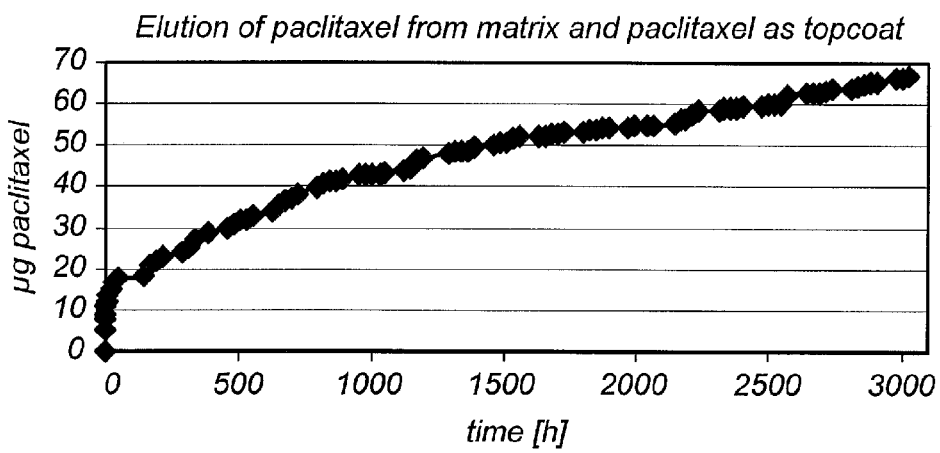

FIG. 9: Elution diagram of paclitaxel embedded into PLGA-matrix and of a layer of undiluted paclitaxel which covers the basis coating completely.

Figure 10:
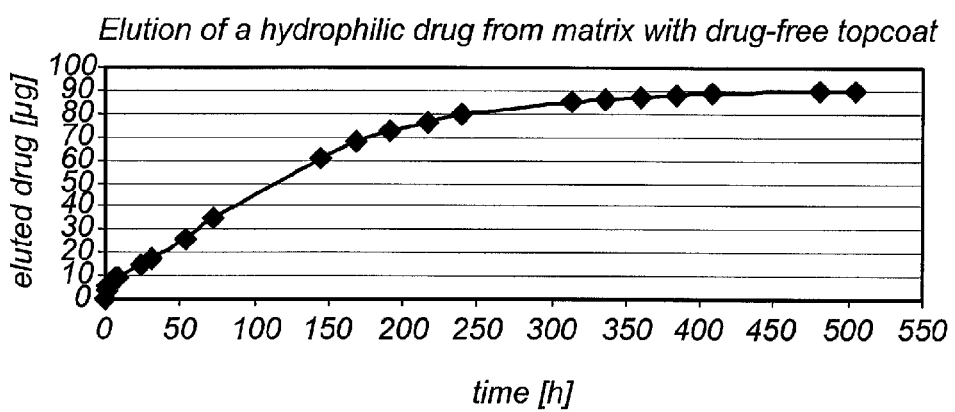

FIG. 10: Elution diagram of a hydrophilic active agent embedded into the matrix and of a suprajacent active agent free polymer (topcoat) which covers the basis coating completely for diffusion control.

Figure 11:
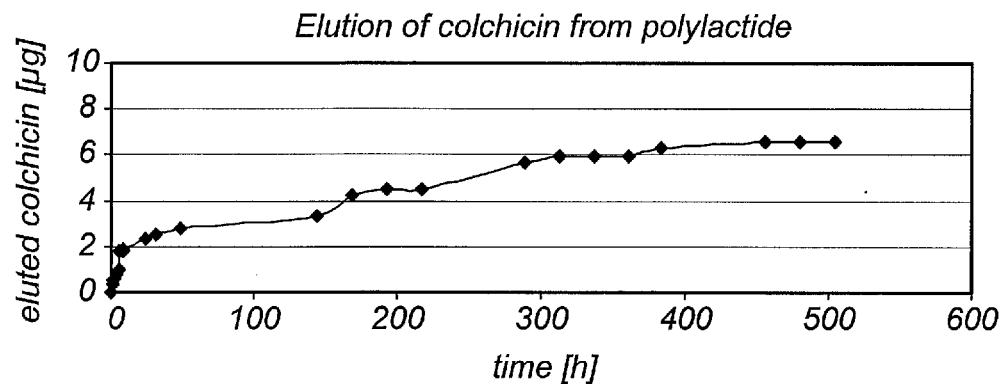

FIG. 11: Elution diagram of colchicine from PLGA-matrix.

Figure 12:
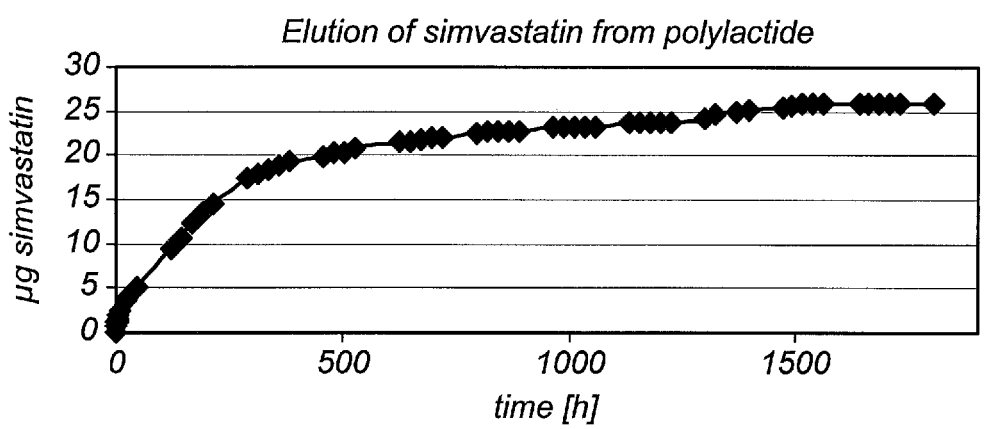

FIG. 12: Elution diagram of simvastatin from PLGA-matrix.

Figure 13:
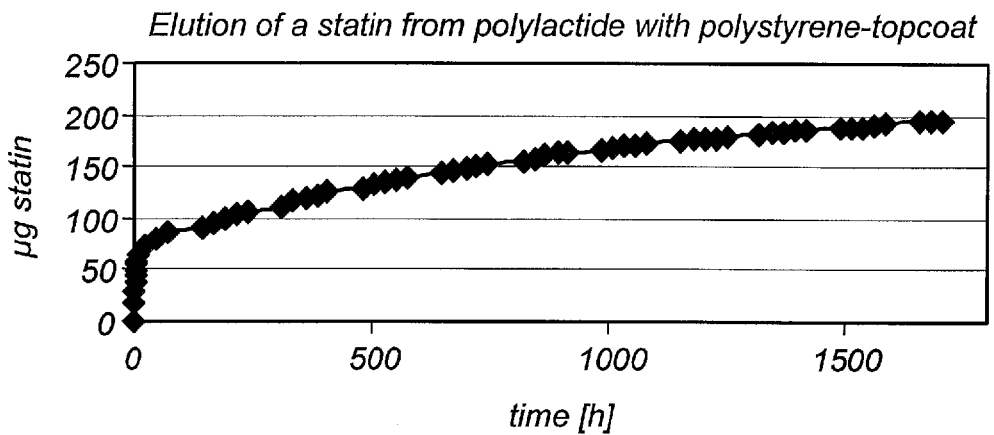

FIG. 13: Elution diagram of a statin from the matrix with polystyrene which completely covers the basis coating as diffusion controlling layer.

Figure 14:
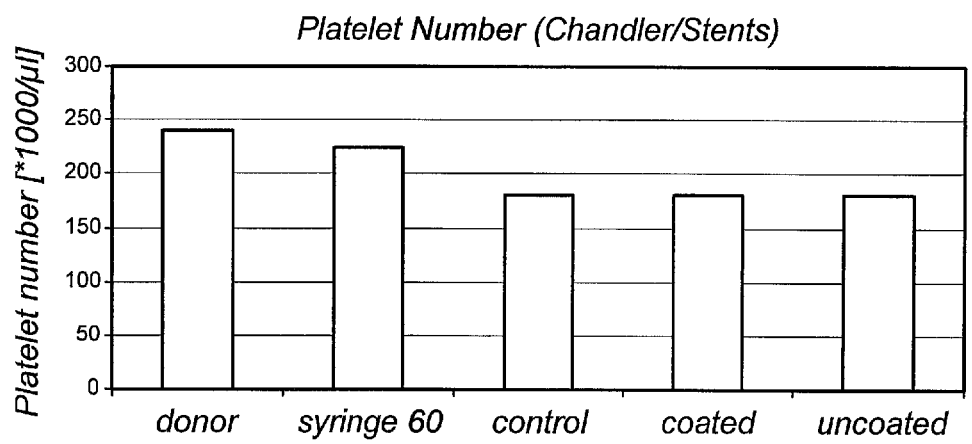

FIG. 14: Comparison of the thrombocyte number (platelet number) in the blood after Chandler loop between coated (coat.) and non coated (unco.) stent as regards the empty tube (control), the platelet number of freshly extracted blood (donor) and after the storage of 60 min in the syringe (syringe 60).

Figure 15:
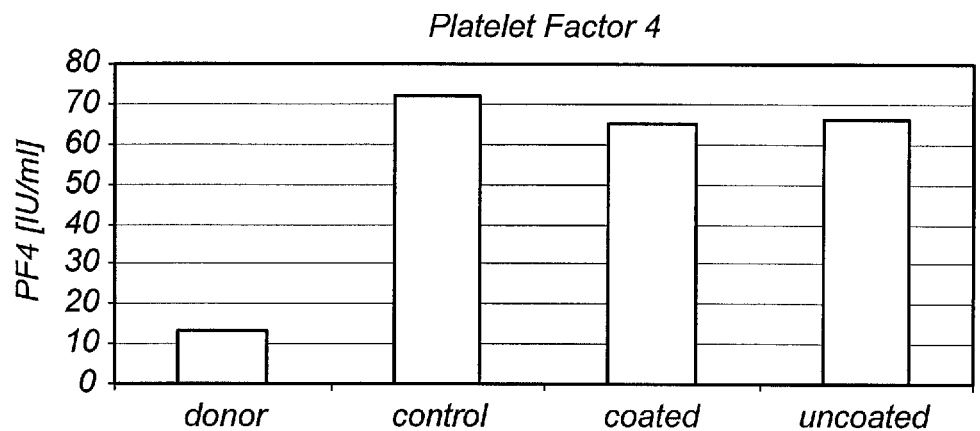

FIG. 15: Comparison of the platelet factor 4 concentration in the freshly extracted blood (donor), in the empty tube (control) after 60 minutes and non coated stents (unco.) with coated (coat.) stent.

Figure 16:
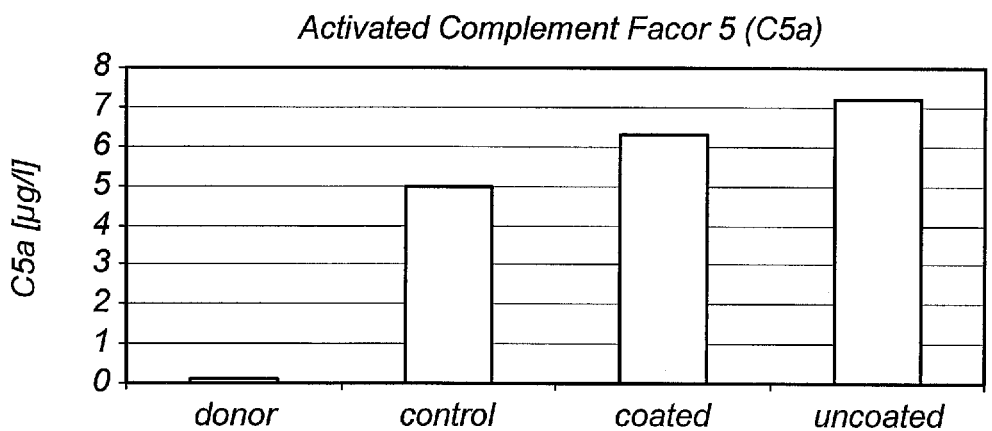

FIG. 16: Comparing diagram to the activated complement factor C5a in the freshly extracted blood (donor), in the empty tube (control) after 60 minutes and non coated (unco.) stents with coated (coat.) stent.

Figure 17:
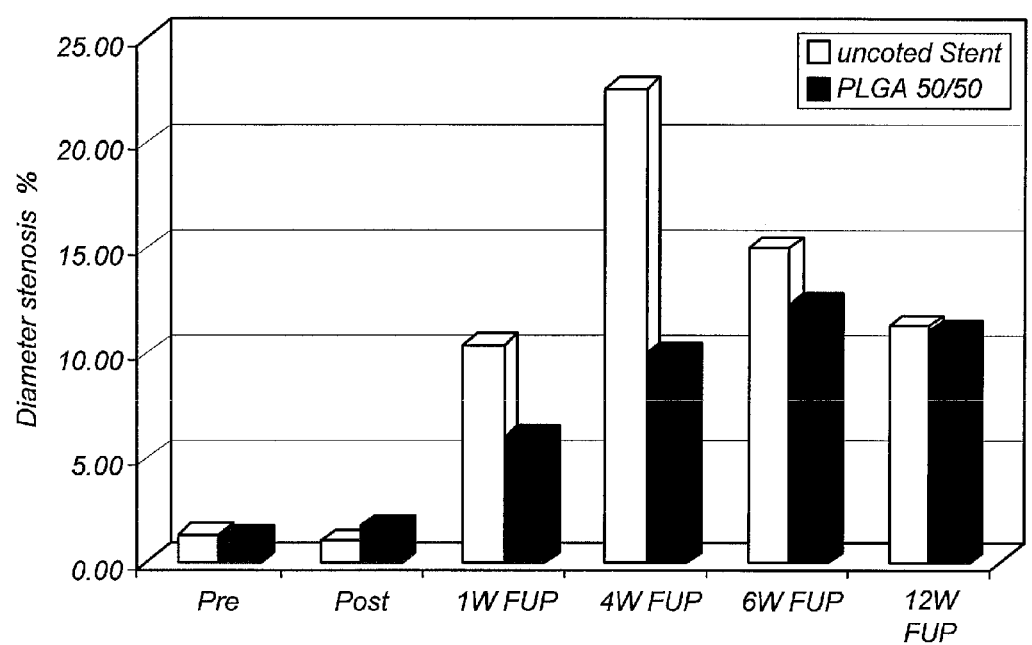

FIG. 17: Schematic presentation of the %-diameter restenosis rate of with completely desulphated and N-reacetylated heparin (Ac-heparin) covalently coated stents and with a 2nd layer of poly(D,L-lactide-co-glycolide) in comparison to the uncoated stent (after 12 weeks of implantation time in the pork). The chronological progression of the stenosis formation in the case of PLGA is shown, whereas "%-diameter restenosis rate" represents the diameter of the vessel related percentually to the initial state directly after implantation of the stent (post). For the experiments six to nine month old domestic porks were used, the vessel diameter was measured before (pre) and after the implantation of the stent (Post) via intravascular ultrasound (IVUS). After one week (1WoFUP), one month (4WoFUP), six weeks (6WoFUP) and after three months (12WoFUP) the stented areas were examined respectively via coronary angiography and with intravascular ultrasound (IVUS). The obtained data show an unexpected amazingly positive effect, which is due to the coating beyond doubt. Although the values of stenosis after three months hardly differ for the uncoated stent and for the coated stent, the reaction of the vessel wall towards the PLGA-coated stent is substantially smoother. After one week the stenosis value lies with 6% significantly below the value of the uncoated implants with 10.4%. The masking of the metal surface results after four weeks even with 10% (an increase of 33%) in a more than factor two lower stenosis rate than the uncoated stent, which reaches after this period of time its maximum value of 22.6% (an increase of 54%). The coated stent shows a maximum after six weeks with only 12.33%. After 12 weeks the values of both systems equal each other with approx. 11%.

Figure 18:
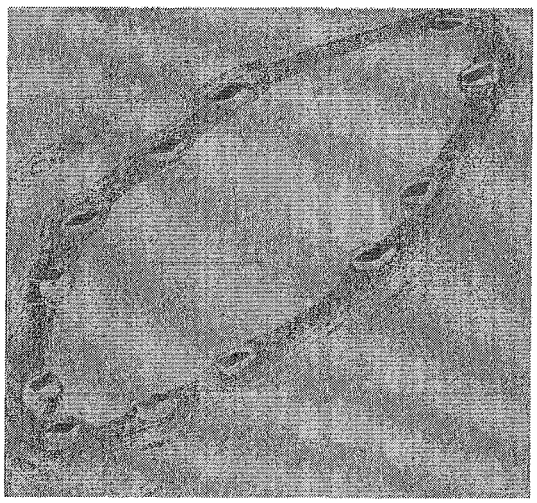
Figure 18:
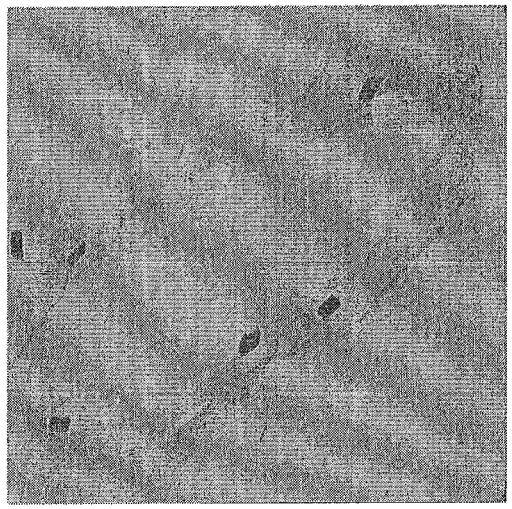
Figure 18:
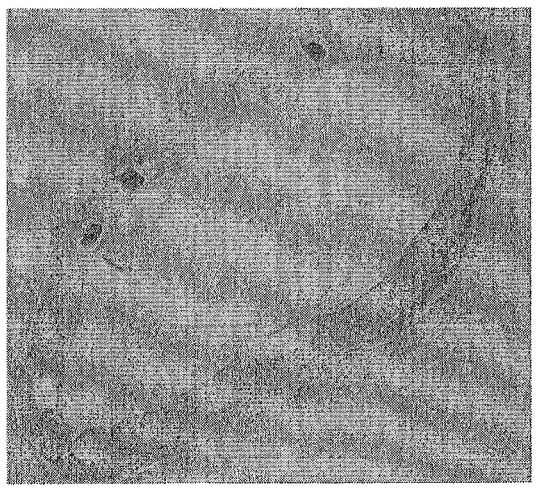
Figure 18:
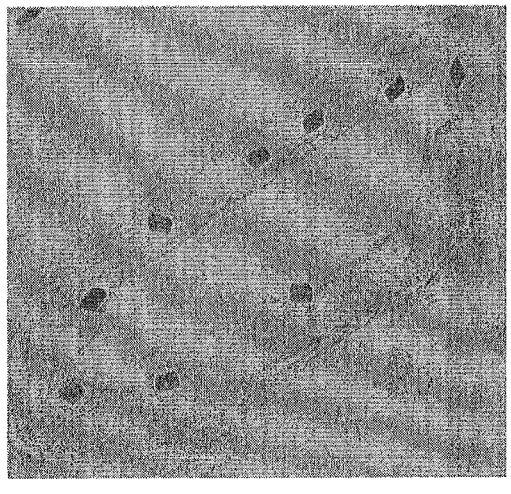

FIG. 18: Pictures of the quantitative coronary angiography of the animal experiments respectively to FIG. 17 after 1 week, 4 weeks, 6 weeks and 3 months of hemocompatibly supplied PLGA-coated stents in the pig.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

The present invention discloses polysaccharides of the general formula Ia

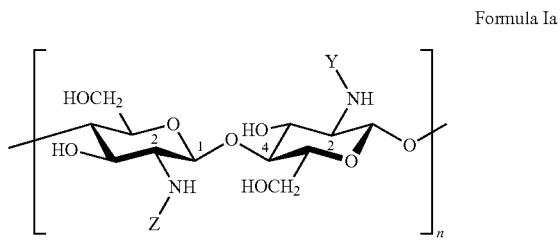

Formula Ia as well as structurally very similar polysaccharides of the general formula Ib

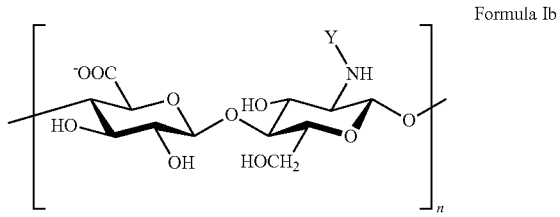

Formula Ib

The polysaccharides according to formula Ia have molecular weights from 2 kD to 400 kD, preferably from 5 kD to 150 kD, more preferably from 10 kD to 100 kD, and particularly preferably from 30 kD to 80 kD. The polysaccharides according to formula Ib have molecular weights from 2 kD to 15 kD, preferably from 4 kD to 13 kD, more preferably from 6 kD to 12 kD, and particularly preferably from 8 kD to 11 kD. The variable n is an integer ranging from 4 to 1050. Preferably, n is an integer from 9 to 400, more preferably from 14 to 260, and particularly preferably an integer between 19 and 210.

The general formulas Ia and Ib represent a disaccharide, which is to be seen as a basic unit of the polysaccharide according to invention and forms the polysaccharide by stringing together said basic unit n times. Said basic unit comprising two sugar molecules does not intend to suggest that the general formulas Ia and Ib only relate to polysaccharides having an even number of sugar molecules. Of course, the general formula Ia and the formula Ib also comprise polysaccharides having an odd number of sugar units. Hydroxy groups are present as terminal groups of the oligosaccharides and polysaccharides, respectively.

The groups Y and Z, independently of each other, represent the following chemical acyl or carboxyalkyl groups: —CHO, —COCH$_3$, —COC$_2$H$_5$, —COC$_3$H$_7$, —COC$_4$H$_9$, —COC$_5$H$_{11}$, —COCH(CH$_3$)$_2$, —COCH$_2$CH(CH$_3$)$_2$, —COCH(CH$_3$)C$_2$H$_5$, —COC(CH$_3$)$_3$, —CH$_2$COO$^-$, —C$_2$H$_4$COO$^-$, —C$_3$H$_6$COO$^-$, —C$_4$H$_8$COO$^-$.

Preferred are the acyl groups—COCH$_3$, —COC$_2$H$_5$, —COC$_3$H$_7$ and the carboxyalkyl groups —CH$_2$COO$^-$, —C$_2$H$_4$COO$^-$, —C$_3$H$_6$COO$^-$. More preferred are the acetyl and propanoyl groups and the carboxymethyl and carboxyethyl groups. Particularly preferred are the acetyl group and the carboxymethyl group.

In addition, it is preferred that the group Y represents an acyl group, and the group Z represents a carboxyalkyl group. It is more preferred if Y is a group —COCH$_3$, —COC$_2$H$_5$ or —COC$_3$H$_7$ and in particular —COCH$_3$. Moreover, it is further preferred if Z is a carboxyethyl or carboxymethyl group, the carboxymethyl group being particularly preferred.

The disaccharide basic unit shown by formula Ia comprises each a substituent Y and a further group Z. This is to make clear that the polysaccharide of the invention comprises two different groups, namely Y and Z. It is important to point out here that the general formula Ia should not only comprise polysaccharides containing the groups Y and Z in a strictly alternating sequence, which would result from stringing together the disaccharide basic units, but also polysaccharides carrying the groups Y and Z in a completely random sequence at the amino groups. Further, the general formula Ia should also comprise polysaccharides containing the groups Y and Z in different numbers. The ratios of the number of Y groups to the number of X groups can be between 70%:30%, preferably between 60%:40%, and particularly preferably between 45%:55%. Especially preferred are polysaccharides of the general formula Ia carrying on substantially half of the amino groups the Y residue and on the other half of the amino groups the Z residue in a merely random distribution. The term "substantially half" means exactly 50% in the most suitable case but should also comprise the range from 45% to 55% and especially from 48% to 52% as well.

Preferred are the compounds of the general formula Ia, wherein the groups Y and Z have the following meanings.

Y=—CHO and Z=—C$_2$H$_4$COO$^-$
Y=—CHO and Z=—CH$_2$COO$^-$
Y=—COCH$_3$ and Z=—C$_2$H$_4$COO$^-$
Y=—COCH$_3$ and Z=—CH$_2$COO$^-$
Y=—COC$_2$H$_5$ and Z=—C$_2$H$_4$COO$^-$
Y=—COC$_2$H$_5$ and Z=—CH$_2$COO$^-$ Especially preferred are the compounds of the general formula Ia, wherein the groups Y and Z have the following meanings:

Y=—CHO and Z=—C$_2$H$_4$COO$^-$
Y=—COCH$_3$ and Z=—CH$_2$COO$^-$

Especially preferred are the compounds of the general formula Ib, wherein Y is one of the following groups: —CHO, —COCH$_3$, —COC$_2$H$_5$ or —COC$_3$H$_7$. Further preferred are the groups —CHO, —COCH$_3$, —COC$_2$H$_5$ and especially preferred is the group —COCH$_3$.

The compounds of the general formula Ib contain only a minor amount of free amino groups. As with the ninhydrine test free amino groups could not be detected anymore, it can be concluded due to the sensitivity of this test, that less than 2%, preferred less than 1% and especially preferred less than 0.5% of all of the —NH—Y groups are present as free amino groups, i.e. at this low percentage of the groups —NH—Y that Y represents hydrogen.

As the polysaccharides of the general formula Ia and Ib contain carboxylate groups and amino groups, the general formulas Ia and Ib also comprise alkali and alkaline earth metal salts of the respective polysaccharides. Thus, alkali metal salts such as the sodium salt, potassium salt, lithium salt or alkaline earth metal salts such as the magnesium salt or calcium salt can be mentioned. Further, with ammonia, primary, secondary, tertiary and quaternary amines, pyridine and pyridine derivatives, ammonium salts, preferably alkyl ammonium salts and pyridinium salts, can be formed. The bases forming salts with the polysaccharides include inorganic and organic bases such as NaOH, KOH, LiOH, CaCO$_3$, Fe(OH)$_3$, NH$_4$OH, tetraalkyl ammonium hydroxides and similar compounds.

Heparan sulphates are ubiquitous on cell surfaces of mammals. Depending on the cell type, they are very different with respect to molecular weight, degree of acetylation and degree of sulfation. Liver heparan sulphate, for example, has a degree of acetylation of approximately 50%, whereas the heparan sulphate from the glycocalyx of endothelial cells can show a degree of acetylation of up to 90% and more. Heparin only shows a very small degree of acetylation of up to 5%. The degree of sulfation of liver heparan sulphate and heparin is ~2 per disaccharide unit, of endothelial cell heparan sulphate nearly 0, and of heparan sulphates from other cell types between 0 and 2 per disaccharide unit.

The following illustration shows a tetrasaccharide unit of a heparin or heparan sulphate with a random distribution of the sulphate groups and a degree of sulfation of 2 per disaccharide unit as typical for heparin:

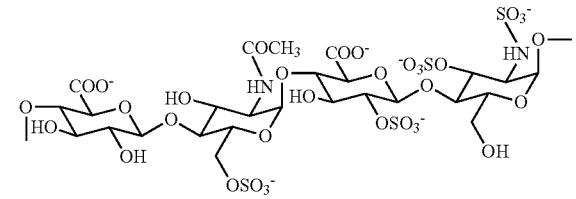

All heparan sulphates have the process of biosynthesis in common with heparin. In this case, first, the core protein with the xylose-containing bond region is built up. It consists of the xylose and two galactose residues connected therewith. To the last one of the two galactose residues, glucuronic acid and galactosamine are then alternately bonded to each other until the respective chain length is achieved. Finally, a multistage enzymatic modification of the common precursor polysaccharide of all heparan sulphates and the heparin by sulfotransferases and epimerases is effected, which, by means of their reactions of varying completeness generate the broad spectrum of various heparan sulphates up to heparin.

Heparin is built up alternately from D-glucosamine and D-glucuronic acid resp. L-iduronic acid, wherein D-glucosamine and D-glucuronic acid are linked in a β-1,4-glycosidic manner (resp. L-iduronic acid in an α-1,4-glycosidic manner) to the disaccharide, which forms the heparin subunits. These subunits, in turn, are linked to each other in a β-1,4-glycosidic manner and lead to the heparin. The position of the sulfonyl groups can change. A tetrasaccharide unit contains an average of 4 to 5 sulfuric acid groups. Heparan sulphate, also referred to as heparitin sulphate, contains, with the exception of liver heparan sulphate, less N- and O-bonded sulfonyl groups than heparin, but more N-acetyl groups.

Figure 3:
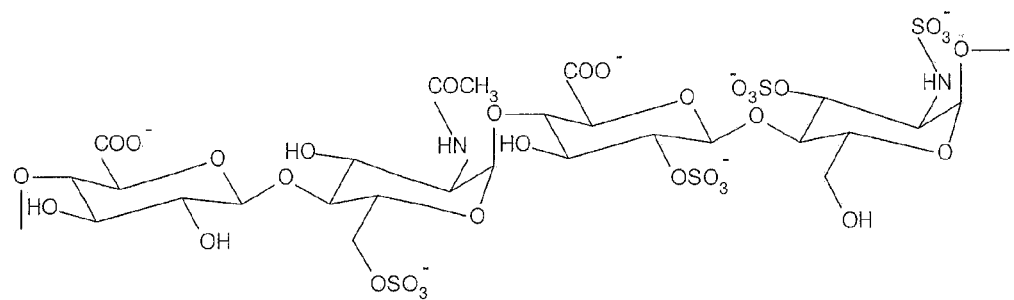
FIG. 3 shows a tetrasaccharide unit of a heparin or heparan sulphate with a random distribution of the sulphate groups and a degree of sulfation of 2 per disaccharide unit as typical for heparin (FIG. 3a). For comparison of the structural similarities
Figure 3:
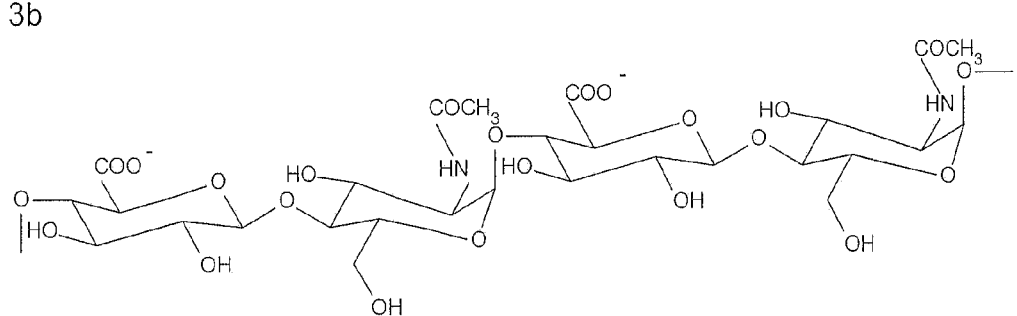
Figure 3:
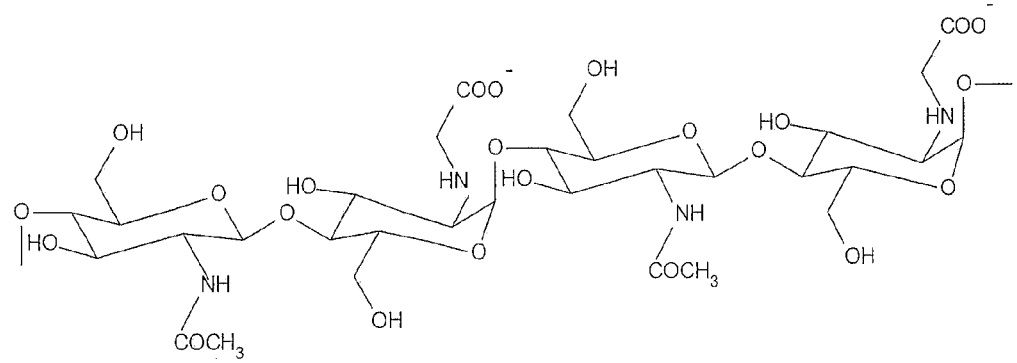

As evident from FIG. 3, the compounds of the general formula Ia (see FIG. 3c as example) and the compounds of the general formula Ib (see FIG. 3b as example) are structurally very similar to the natural heparan sulphate of endothelial cells, but prevent the initially described disadvantages in using endothelial cell heparan sulphates.

For the antithrombotic activity a special pentasaccharide unit is made responsible which can be found in commercial heparin preparatives in about every 3rd molecule. Heparin preparations of different antithrombotic activity can be produced by special separation techniques. In highly active, for example by antithrombin-III-affinitychromatography obtained preparations ("High-affinity"-heparin) this active sequence is found in every heparin molecule, while in "No-affinity"-preparations no characteristical pentasaccharide sequences and thus no active inhibition of coagulation can be detected. Via interaction with this pentasaccharide the activity of antithrombin III, an inhibitor of the coagulation key factor thrombin, is essentially exponentiated (bonding affinity increase up to the factor $2\times10^3$) [Stiekema J. C. J.; *Clin Nephrology* 26, Suppl. No. 1, S3-S8, (1986)].

The amino groups of the heparin are mostly N-sulphated or N-acetylated. The most important O-sulphation positions are the C2 in the iduronic acid as well as the C6 and the C3 in the glucosamine. For the activity of the pentasaccharide onto the plasmatic coagulation basically the sulphate group on C6 is made responsible, in smaller proportion also the other functional groups.

Surfaces of medicinal implants coated with heparin or heparansulphates are and remain only conditionally hemocompatible by the coating. The heparin or heparansulphate which is added onto the artificial surface loses partially in a drastic measure its antithrombotic activity which is related to a restricted interaction due to steric hindrence of the mentioned pentasaccharide units with antithrombin III.

Because of the immobilisation of these polyanionic substances a strong adsorption of plasma protein on the heparinated surface is observed in all cases what eliminates on the one hand the coagulation suppressing effect of heparin resp. of heparansulphates and initialises on the other hand specific coagulation processes by adherent and hereby tertiary structure changing plasma proteins (e.g. albumin, fibrinogen, thrombin) and thereon adherent platelets.

Thus a correlation exists on the one hand between the limited interaction of the pentasaccharide units with antithrombin III by immobilisation on the other hand depositions of plasma proteins on the heparin-resp. heparansulphate layer on the medicinal implant take place, which leads to the losses of the antithrombotic properties of the coating and which can even turn into the opposite, because the plasma protein adsorption that occurs during a couple of seconds leads to the loss of the anticoagulating surface and the adherent plasma proteins change their tertiary structure, whereby a thrombonegeous surface arises. Surprisingly it could be detected that the compounds of the general formulas Ia and Ib, despite of the structural differences to the heparin resp. heparansulphate, still show the hemocompatible properties of heparin and additionally during the immobilisation of the compounds of the general formulas Ia and Ib no noteworthy depositions of plasma proteins which represent an initial step in the activation of the coagulation cascade could be observed. The hemocopatible properties of the compounds according to invention still remain also after their immobilisation on artificial surfaces.

Further on it is supposed that the sulphate groups of the heparin resp. the heparansulphates are necessary for the interaction with antithrombin III and impart thereby the heparin resp. the heparansulphate the anticoagulatory effect. The inventive compounds according to formula Ib as well as the compounds according to formula Ia are not actively coagulation suppressive, i.e. anticoagulative, due to an almost complete desulphation the sulphate groups of the compounds of the general formulas Ib are removed up to a low amount of below 0.2 sulphate groups per disaccharide unit.

The compounds of the invention according to the general formula Ib can be made from heparin or heparan sulphates by first substantially entirely desulfating and then substantially entirely N-acylating the polysaccharide. The term "substantially entirely desulphated" refers to a degree of desulfation of more than 90%, preferred more than 95%, and particularly preferred more than 98%. The degree of desulfation can be determined according the so-called ninhydrine test, which detects free amino groups. Desulfation is effected to such an extent that a color reaction is no longer obtained with DMMB (dimethylmethylene blue). This color test is suitable for detecting sulphated polysaccharides; however, the detection limit thereof is not known in the literature of the art. The desulfation can, for example, be carried out by heating the pyridinium salt in a solvent mixture. In particular, a mixture of DMSO, 1,4-dioxane and methanol proved to be suitable.

Heparansulphates as well as heparin were desulphated via total hydrolysis and subsequently reacylated. Thereafter the number of sulphate groups per disaccharide unit (S/D) was determined by $^{13}$C-NMR. The following table 1 shows these results on the example of heparin and desulphated, reacetylated heparin (Ac-heparin).

TABLE 1

Distribution of functional groups per disaccharide unit on the example of heparin and Ac-heparin as determined by 13C-NMR-measurements.

|  | 2-S | 6-S | 3-S | NS | N—Ac | NH$_2$ | S/D |
|---|---|---|---|---|---|---|---|
| Heparin | 0.63 | 0.88 | 0.05 | 0.90 | 0.08 | 0.02 | 2.47 |
| Ac-heparin | 0.03 | 0 | 0 | 0 | 1.00 | — | 0.03 |

2-S, 3-S, 6-S: sulphate groups in position 2, 3, 6 respectively
NS: sulphate groups on the amino groups
N—Ac: acetyl groups on the amino groups
NH$_2$: free amino groups
S/D: sulphate groups per disaccharide unit A sulphate content of about 0.03 sulphate groups/disaccharide unit (S/D) in case of Ac-heparin in comparison with about 2.5 sulphate groups/disaccharide unit in case of heparin was reproducibly obtained.

As described above the difference in the sulphate contents of heparin resp. heparansulphates and the compounds of the general formulas has a considerable influence on the activity adverse to antithrombin III and the coagulatory effects of these compounds.

The compounds of the general formulas Ia and Ib have a content of sulphate groups per disaccharide unit of less than 0.2, preferred less than 0.07, more preferred less than 0.05 and especially preferred less than 0.03 sulphate groups per disaccharide unit.

By the removal of the sulphate groups of heparin, to which the active coagulation suppressive working mechanism is accredited to, one receives for a surface refinement suitable hemocompatible, coagulation inert oligo-resp. polysaccharide which on the one hand has no active role in the coagulation process and which on the other hand is not detected by the coagulation system as foreign surface. This coating imitates successfully the nature given highest standard of hemocompatibility and passivity against the coagulation active components of the blood.

The examples 5 and 6 clarify, that surfaces, which are coated with the compounds according to invention according to the general formulas Ia and/or Ib, especially which are coated covalently, result in a passivative, athrombogeneous, hemocompatible, antiproliferative and/or antiinflammatory coating. This is clearly proven by the example of the Ac-heparin.

The term "substantially entirely N-acylated" refers to an N-acylating degree of more than 94%, preferably more than 97%, and particularly preferably more than 98%. The acylation is effected in such a complete manner that the ninhydrine detection of free amino groups does no longer show any color reaction. As acylation agents, carboxylic acid chlorides, bromides or anhydrides are used preferably. Acetic acid anhydride, propionic acid anhydride, butyric acid anhydride, acetic acid chloride, propionic acid chloride or butyric acid chloride, for example, are suitable for preparing the compounds according to the invention. Carboxylic acid anhydrides are particularly suitable as acylation agents.

As the solvent, in particular for the carboxylic acid anhydrides, deionized water is used, preferably together with a cosolvent, which is added in an amount of 10 to 30 volume percent.

As cosolvents, methanol, ethanol, DMSO, DMF, acetone, dioxane, THF, acetic acid ethyl ester and other polar solvents are suitable. If carboxylic acid halides are used, polar water-free solvents such as DMSO or DMF are preferably used.

As the solvent deionized water is used, preferably together with a cosolvent, which is added in an amount of 10 to 30 volume percent. As cosolvents, methanol, ethanol, DMSO, DMF, acetone, dioxane, THF, acetic acid ethyl ester and other polar solvents are suitable.

The compounds of the invention according to the general formula Ia have a carboxylate group on half of the sugar molecules, and a N-acyl group on the other half.

Such compounds can also be made from the polysaccharides hyaluronic acid, dermatan sulphate, chondroitin sulphate. Differencies to heparin and heparansulphate result from the connection of the monosaccharides, which are here not present in a 1,4-glycosidic but 1,3-glycosidic connection. The disaccharides are again connected to each other 1,4-glycosidically. In the case of the also in the blood coagulation antithrombotically active dermatan sulphates [Biochem. J. 289, 313-330 (1993)] and the chrondoitin sulphates N-acetyl-glucosamine is substituted by N-acetylgalactosamine, which differ in the steric position of the hydroxyl group at the C-atom 4.

Due to their related structure the polysaccharides are assigned according to the present differencies as follows:
Type 1) Uronic Acid—Galactosamine Type (HexA-GalN)$_n$:

Hereto accounted are chondroitin sulphate and dermatan sulphate. Typical for this group ist the β-1,3-glycosidic bonding of the uronic acid to the galactosamine. Galactosamine is bound on its part β-1,4-glycosidically to the next uronic acid. Dermatan sulphate differs from chondroitin sulphate by a high amount of another also in heparin and heparan sulphate occurring uronic acid, the L-iduronic acid. The sulphation degree of chondroitin sulphate is at 0.1 to 1.3 sulphate groups per disaccharide. Dermatan sulphate has with 1.0 to 3.0 sulphate groups per disaccharide an averagely higher sulphation degree as chondroitin sulphate and thereby reaches heparin like values. The amino groups are N-acetylated.

The desulphation and N-reacetylation leads here as in the case of heparin and heparan sulphate to compounds, which are also suitable for the use as athrombogeneous coating.
Type 2) Uronic Acid—Glucosamine Type (HexA-GlcN)$_n$:

Hereto accounted are heparin, heparan sulphate and hyaluronan. Heparin and heparan sulphate are solely 13-1,4-bound, whilst in hyaluronan, which is also accounted to this type, the monosaccharids D-glucuronic acid and D-glucosamine are 13-1,3-bound monosaccharids. This polysaccharide has as only polysaccharide no sulphate groups and is N-acetylated. The molecular weight reaches in comparison to heparin and heparan sulphate maximum values up to 8000 kD. The reduction of the chain length and the maintaining of the acetyl groups resp. the N-reacetylation leads to a structure, which is distinguishable from the formula Ib only by the 13-1,3-glycosidic connection of the monosaccharids.
Further Compounds can be Prepared Also from Chitin or Chitosan.

Chitin is a nitrogen-containing polysaccharide, the monomer units of which consist of N-acetyl-D-glucosamine, which are linked in a 13-1,4-glycosidic manner. This results in linear polymers consisting of about 2,000 sugar units and having a molecular weight of about 400,000 g/mol. Chitin shows a very poor solubility and is almost insoluble in water, organic solvents and dilute acids or dilute bases. Mixing with strong acids leads to hydrolysis, where D-glucosamine and acetic acid are produced. The treatment with strong bases, however, leads to chitosan and acetate.

Chitosan can easily be produced by the saponification of chitin. Chitosan consists of β-1,4-glycosidically linked glucosamine (2-amino-2-deoxy-D-glucose). Chitosan is known for its film forming properties, and is further used as a basic material for ion exchangers and as an agent for reducing the cholesterol level in the blood serum and for weight reduction.

Figure 1:
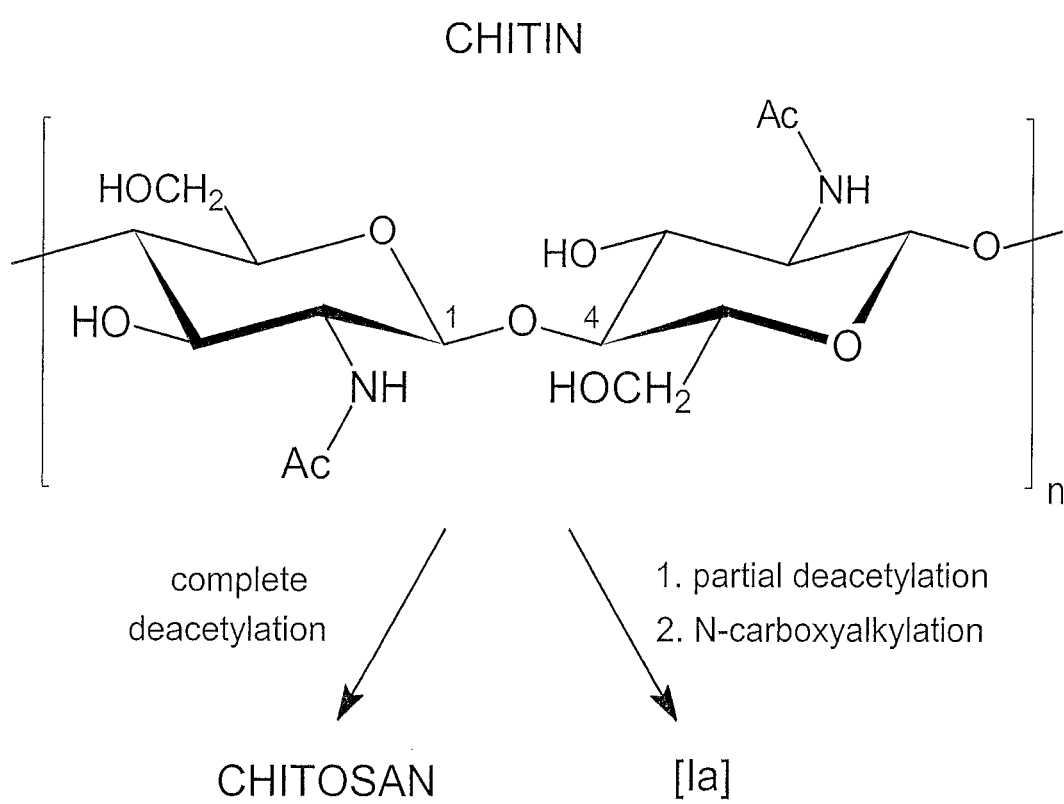
FIG. 1 shows a disaccharide structure fragment of chitin which can be transformed into chitosan by basic hydrolysis, or into the compounds of the general formula Ia by partial deacetylation and subsequent N-carboxyalkylation.
Figure 2:
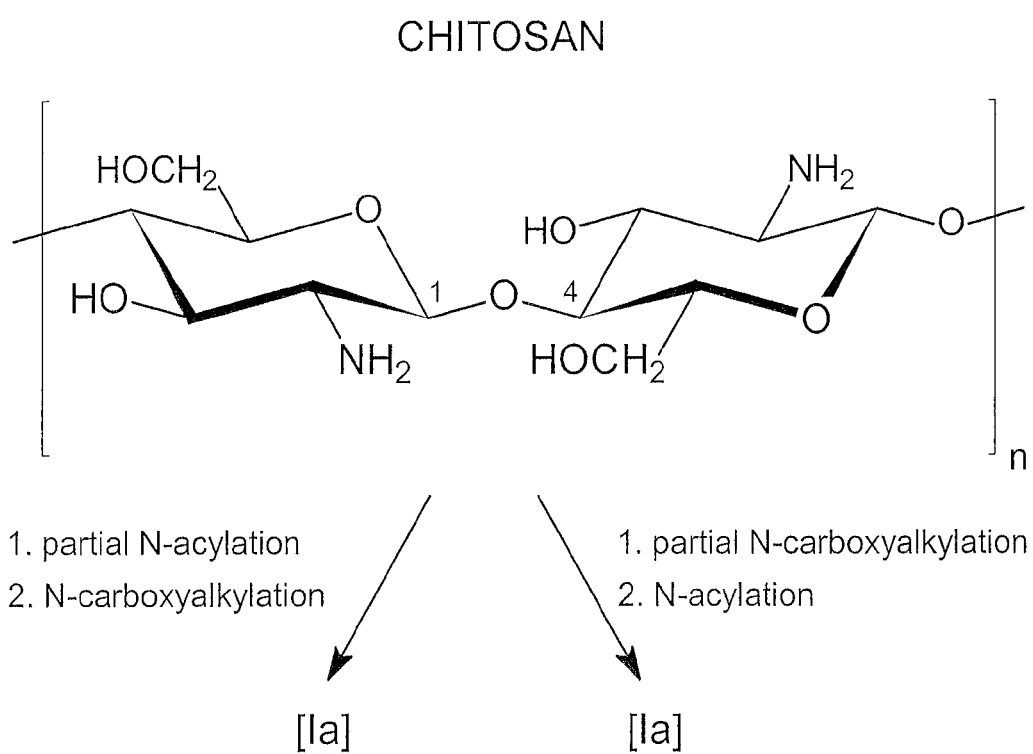
FIG. 2 shows a disaccharide structure fragment of chitosan, which can be transformed into the compounds of the general formula Ia by partial N-acylation and subsequent N-carboxyalkylation or by partial N-carboxyalkylation and subsequent N-acylation.

The substances according to the invention of the general formula Ia can be made from chitin by partially deacetylating chitin by means of strong bases and then monocarboxyalkylating the free amino groups (see FIG. 1). The deacetylation degree, i.e. the amount of demasked primary amino groups, can be determined volumetrically. The quantitative detection of the free amino groups is effected by means of the ninhydrine reaction. Depending on the way the experiment is carried out, deacetylation degrees of 20 to 80% can be obtained. Deacetylation degrees of 40 to 60% are preferred, 45 to 55% are particularly preferred.

By this way of synthesis, polysaccharides can be obtained the sugar units of which contain either an N-acetyl group or an N-carboxyalkyl group in a merely random distribution.

Chitosan, which is easily accessible by the basic hydrolysis of the N-acetyl groups of the chitin (see FIG. 1), equally serves as a starting material for the synthesis of the polysaccharides according to formula Ia.

Chitosan only has very few N-acetyl groups. Thus, the compounds according to the invention can, on the one hand, be obtained by carboxyalkyating substantially the half of the free amino groups in a first step, and then acylating the remaining free amino groups, or by first carrying out the acylation and then reacting the remaining free amino groups with a suitable carboxyalkylation agent. It is preferred if substantially the half of the amino groups is acylated and the remaining half is carboxyalkylated.

"Partially N-acylated chitosan" refers to an N-acylation degree of 30-70%, preferably of 40-60%, and particularly preferably of 45-55%. Particularly preferred are chitosan derivates carrying the Y residue on substantially the half of the amino groups, and on the other half of the amino groups the Z residue in a merely random distribution. The term "substantially the half" means exactly 50% in the most suitable case, but should also include the range of 45% to 55%. The carboxyalkylation and acylation degrees can be determined by means of $^{13}$C-NMR, for example (deviation tolerance ±3%).

Due to the fact that in a first reaction step a certain number of the free amino groups are acylated or carboxyalkylated, this inevitably results in a completely random distribution of the acyl groups resp. carboxyalkyl groups in the polysaccharide of the general formula Ia. The formula Ia thus is only intended to show a disaccharide unit of the polysaccharides according to the invention, but not determine an alternating sequence of the acyl groups and carboxyalkyl groups.

The following illustration shows a typical tetrasaccharide unit of an N-carboxymethylated, N-acetylated chitosan:

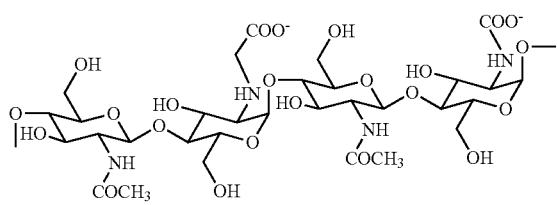

The present invention describes the use of the compounds of the general formulas Ia and/or Ib as well as salts of said compounds for the coating, in particular a hemocompatible coating of natural and/or artificial surfaces. "Hemocompatible" refers to the property of the compounds according to the invention, which means not to interact with the substances of the blood coagulation system or the blood platelets and thus not to trigger the blood coagulation cascade.

In addition, the invention discloses oligosaccharides and/or polysaccharides for the hemocompatible coating of surfaces. Preferred are polysaccharides within the molecular weight limits mentioned above. One of the remarkable features of the oligosaccharides and/or polysaccharides used is, that they contain large amounts of the sugar unit N-acylglucosamine or N-acylgalactosamine. This means that 40-60%, preferred 45-55% and especially preferred 48-52% of the sugar units are N-acylglucosamine or N-acylgalactosamine, and substantially the remaining sugar units each have a carboxyl group. Thus, usually more than 95%, preferably more than 98%, of the oligosaccharides and/or polysaccharides consist of only two sugar units, one sugar unit carrying a carboxyl group and the other one an N-acyl group.

One sugar unit of the oligosaccharides and/or polysaccharides is N-acylglucosamine resp. N-acylgalactosamine, preferably N-acetylglucosamine resp. N-acetylgalactosamine, and the other one is uronic acid, preferably glucuronic acid and iduronic acid.

Preferred are oligosaccharides and/or polysaccharides substantially consisting of the sugar glucosamine resp. galactosamine, substantially the half of the sugar units carrying an N-acyl group, preferably an N-acetyl group, and the other half of the glucosamine units carrying a carboxyl group directly bonded via the amino group or bonded via one or more methylenyl groups. These carboxylic acid groups bonded to the amino group are preferably carboxymethyl or carboxyethyl groups. Further are preferred oligosaccharides and/or polysaccharides, wherein substantially the half, i.e. 48-52%, preferred 49-51% and especially preferred 49.5-50.5%, consists of N-acyl glucosamine resp. N-acyl galactosamine, preferably of N-acetyl glucosamine or N-acetyl galactosamine, and substantially the other half thereof consists of an uronic acid, preferably glucuronic acid and iduronic acid. Particularly preferred are oligosaccharides and/or polysaccharides showing a substantially alternating sequence (i.e. despite of the statistic deviation ratio in the case of the alternating connection) of the two sugar units. The ratio of the deviated connections should be under 1%, preferred under 0.1%.

Surprisingly, it has been shown that, for the uses according to the invention, in particular substantially desulphated and substantially N-acylated heparin as well as partially N-carboxyalkylated and N-acylated chitosan as well as desulphated and substantially N-acylated dermatan sulphate, chondroitin sulphate and also chain length reduced hyaluronic acid are especially suitable. In particular, N-acetylated heparin as well as partially N-carboxymethylated and N-acetylated chitosan are suitable for the hemocompatible coating.

The desulphation and acylation degrees defined by "substantially" were already defined more above. The term "substantially" is intended to make clear, that statistic deviations have to be taken into consideration. A substantially alternating sequence of the sugar units means, that as a rule two equal sugar units are not bonded to each other, but does not completely exclude such an erroneous linkage. Correspondingly, "substantially the half" means nearly 50%, but permits slight variations, because especially with biosynthetically produced macromolecules, the most suitable case is never achieved, and certain deviations have always to be taken into consideration as enzymes do not work perfectly and catalysis usually involves a certain rate of errors. In the case of natural heparin, however, there is a strictly alternating sequence of N-acetyl glucosamine and uronic acid units (instead of glucuronic).

Furthermore, a process for the hemocompatible coating of surfaces is disclosed, which are intended for direct blood contact. In said process, a natural and/or artificial surface is provided, and the oligosaccharides and/or polysaccharides described above are immobilized on said surface.

The immobilisation of the oligosaccharides and/or polysaccharides on these surfaces can be achieved via hydrophobic interactions, van der Waals forces, electrostatic interactions, hydrogen bonds, ionic interactions, cross-linking of the oligosaccharides and/or polysaccharides and/or by covalent bonding onto the surface. Preferred is the covalent linkage of the oligosaccharides and/or polysaccharides (side-on bonding), more preferred the covalent single-point linkage (side-on bonding) and especially preferred the covalent end-point linkage (end-on bonding).

Any natural and/or artificial surfaces of medical products can be used here such as surfaces of prostheses, organs, vessels, aortas, cardiac valves, tubes, organ replacement parts, implants, fibers, hollow fibers, stents, hypodermic needles, syringes, membranes, conserves, blood containers, titer plates, pacemakers, adsorber media, chromatography media, chromatography columns, dialyzers, connection parts, sensors, ventiles, centrifuge chambers, heat exchangers, endoscopes, filters, pump chambers as well as other surfaces, which should have hemocompatible properties. The term "medical products" is to be understood widely and refers especially to the surfaces of such products, which come into contact with blood shortly (e.g. endoscopes) or permanently (e.g. stents).

In the following the coating methods according to invention are described. Biological and/or artificial surfaces of medical devices can be provided with a hemocompatible coating by means of the following method:

a) providing a surface of a medical device and
b) deposition of at least one oligosaccharide and/or polysaccharide according to formula Ia or Ib, and/or
at least one oligosaccharide and/or polysaccharide, which contains between 40% and 60% the sugar unit N-acyl glucosamine or N-acyl galactosamine and the remaining sugar units substantially contain one carboxyl group per sugar unit.

"Deposition" shall refer to at least partial coating of a surface with the corresponding compounds, wherein the compounds are deposited and/or introduced and/or immobilized or anyhow anchored on and/or in the subjacent surface.

Under "substantially the remaining sugar building units" is to be understood, that 93% of the remaining sugar building units, preferred 96% and especially preferred 98% of the remaining 60%-40% of the sugar building units bear a carboxyl group.

An uncoated and/or non hemocompatible surface is preferably provided. "non-hemocompatible" surfaces shall refer to such surfaces that can activate the blood coagulatory system, thus are more or less thrombogeneous.

An alternative embodiment comprises the steps:
a) providing surface of a medical device and
b') deposition of a biostable layer onto the surface of the medical device
or
a) providing surface of a medical device and
b) deposition of at least one oligosaccharide and/or polysaccharide according to formula Ia or Ib,
and/or
at least one oligosaccharide and/or polysaccharide, which contains between 40% and 60% the sugar unit N-acyl glucosamine or N-acyl galactosamine and the remaining sugar units substantially contain one carboxyl group per sugar unit.
b') deposition of a biostable layer onto the surface of the medical device and
d') deposition of a further hemocompatible layer of at least one inventive oligosaccharide and/or polysaccharide according to formula Ia or Ib,
and/or
at least one oligosaccharide and/or polysaccharide, which contains between 40% and 60% the sugar unit N-acyl glucosamine or N-acyl galactosamine and the remaining sugar units substantially contain one carboxyl group per sugar unit.

The last-mentioned embodiment makes sure, even in the case of mechanical damage of the polymeric layer and therewith also of the exterior hemocompatible layer, e.g. due to inappropriate transport or complicated conditions during the implantation, that the surface coating does not lose its characteristic of being blood compatible.

Under "biological and artificial" surface is the combination of an artificial medical device with an artificial part to be understood, e.g. a pork heart with an artificial heart valve.

The single layers are deposited preferably by dipping or spraying methods, whereas one can deposit at the same time with the deposition of one layer also another or more active agents onto the medical device surface, which is then implemented in the respective layer covalently and/or adhesively bound. In this way one or more active agents can be deposited at the same time with the deposition of a hemocompatible layer onto the medical device.

The active agents as well as the substances, which can be used for a biostable or biodegradable layer, are itemized more below.

Onto this first biostable or hemocompatible layer it is then possible in an additional non compulsory step c) to deposit an active agent layer of one or more active agents. In a preferred embodiment the active agent or agents are bound covalently on the subjacent layer. Also the active agent is preferably deposited by dipping or spraying methods.

After the step b) or the step c) an additional step d) can follow, which comprises the deposition of at least one biodegradable layer and/or at least one biostable layer onto the hemocompatible layer resp. the active agent layer.

According to the alternative embodiment after step b') or step c) a step d') can follow, which comprises the deposition or immobilisation of at least one oligosaccharide and/or polysaccharide according to invention according to formula Ia or Ib and/or at least one oligosaccharide and/or polysaccharide, which contains between 40% and 60% the sugar unit N-acyl glucosamine or N-acyl galactosamine and the remaining sugar units substantially contain one carboxyl group per sugar unit, as hemocompatible layer. Preferably after step b') the step d') follows.

After step d) resp. d') the deposition of another active agent layer of one or more active agents can take place into or onto the subjacent biodegradable and/or biostable layer or the hemocompatible layer.

Additionally to the deposited active agent layers the biostable, biodegradable and/or hemocompatible layers can contain further active agents, which were deposited together with the biostable and/or biodegradable substances or the hemocompatible oligosaccharides and/or polysaccharides on the medical device and are contained in the respective layers.

According to a preferred embodiment the biostable layer is covalently and/or adhesively bound on the surface of the medical device and completely or incompletely covered with a hemocompatible layer, which (preferably covalently) is bound to the biostable layer.

Preferably the hemocompatible layer comprises heparin of native origin or regioselectively synthesized derivatives of different sulphation coefficients (sulphation degrees) and acylation coefficients (acylation degrees) in the molecular weight range of the pentasaccharide which is responsible for the antithrombotic activity, up to the standard molecular weight of the purchasable heparin of 13 kD, heparansulphate and its derivatives, oligo- and polysaccharides of the erythrocytic glycocalix, desulphated and N-reacetylated heparin, N-carboxymethylated and/or partially N-acetylated chitosan as well as mixtures of these substances.

Subject of the invention are also medical devices, which are hemocompatibly coated according to one of the herein mentioned methods.

Furthermore subject of the invention are medical devices, whereas the surface of the medical devices is covered directly or via at least one interjacent biostable and/or biodegradable layer and/or active agent layer with a hemocompatible layer, which consists of at least one oligosaccharide and/or polysaccharide, which contains between 40% and 60% the sugar unit N-acyl glucosamine or N-acyl galactosamine and the remaining sugar units substantially contain one carboxyl group per sugar unit.

According to a preferred embodiment under the hemocompatible layer of the afore-mentioned oligosaccharides and/or polysaccharides is at least one biostable layer present, which is additionally preferred covalently bound to the surface of the medical device.

It is further preferred, if on the hemocompatible layer at least one biostable and/or at least one biodegradable layer is present, which covers the hemocompatible layer completely or incompletely. Especially preferred is a biodegradable layer, which covers the hemocompatible layer.

A further preferred embodiment contains between the biostable lower layer and the subjacent hemocompatible layer an active agent layer of at least one antiproliferative, antiinflammatory and/or antithrombotic active agent, which is bound covalently and/or adhesively to the hemocompatible layer. Alternatively to the active agent layer or additionally to the active agent layer the lower biostable and/or upper hemocompatible layer can contain further active agents, which are deposited preferably together with the deposition of the respective layer.

Basically every layer, i.e. a biostable layer, a biodegradable layer and a hemocompatible layer can contain one or more antiproliferative, antiinflammatory and/or antithrombotic active agents and moreover between the afore-mentioned layers active agent layers of one or more active agents can be present. Preferred are coating systems of two layers, a biostable and a hemocompatible layer, whereas the hemocompatible layer is the external layer and both layers can contain one or more active agents. Further it is preferred if on or under the hemocompatible layer an active agent layer of one or more active agents is present. Also preferred are three-layer systems, which consist of a biostable, biodegradable and hemocompatible layer. Thereby preferably the lowest layer is a biostable layer. Additionally one or two active agent layers are possible. It is also possible to deposit two active agent layers directly above each other. In a further preferred embodiment at least one active agent is bound covalently on or in a layer.

Preferably used in the methods of coating and on the medical devices as active agents are tacrolimus, pimecrolimus, PI88, thymosin α-1, PETN (pentaerythritol tetranitrate), baccatin and its derivatives, docetaxel, colchicin, paclitaxel and its derivatives, trapidil, α- and β-estradiol, dermicidin, tialin (2-methylthiazolidine-2,4-dicarboxylic acid), tialin-sodium (sodium salt of tialin), simvastatine, macrocyclic suboxide (MCS) and its derivatives, sirolimus, tyrphostines, D24851, colchicin, fumaric acid and fumaric acid esters, activated protein C (aPC), interleucine-1β inhibitors, and melanocyte-stimulating hormone (α-MSH) as well as mixtures of these active agents.

The natural and/or artificial surfaces of the medical devices, which are coated according to the herein described methods with a hemocompatible layer of the inventive oligosaccharide and/or polysaccharide resp. the oligosaccharides and/or polysaccharides which contain between 40% and 60% the sugar unit N-acyl glucosamine or N-acyl galactosamine and the remaining sugar units substantially contain one carboxyl group per sugar unit, are especially suitable as implants and organ replacement parts, respectively, which are in direct contact with the blood circuit and the blood. The medical devices coated according to invention are especially suitable, but not only, for the direct and permanent blood contact, but show surprisingly also the characteristic to reduce or even to prevent the adhesion of proteins onto such-like coated surfaces.

The adhesion of plasma proteins on foreign surfaces which come in contact with blood is an essential and initial step for the further events concerning the recognition and the implementing action of the blood system.

This is for example important in the in vitro diagnostics from body fluids. Thus the deposition of the inventive coating prevents or at least reduces for example the unspecific adhesion of proteins on micro-titer plates or other support mediums which are used for diagnostic detection methods, that disturb the generally sensitive test reactions and can lead to a falsification of the analysis result.

By use of the coating according to invention on adsorption media or chromatography media the unspecific adhesion of proteins is also prevented or reduced, whereby better separations can be achieved and products of greater purity can be generated.

Especially stents are coated according to the inventive methods. The implantation of stents using balloon dilatation of occluded vessels increasingly established in the last years. Although stents decrease the risk of a renewed vessel occlusion they are until now not capable of preventing such restenoses completely.

An exact conceptual description of restenosis cannot be found in the technical literature. The most commonly used morphologic definition of the restenosis is the one which defines the restenosis after a successful PTA (percutaneous transluminal angioplasty) as a reduction of the vessel diameter to less than 50% of the normal one. This is an empirically defined value of which the hemodynamic relevance and its relation to clinical pathology lacks of a massive scientific basis. In practical experience the clinical aggravation of a patient is often viewed as a sign for a restenosis of the formerly treated vessel segment.

There are three different reasons for the restenosis caused by the stent:

a.) During the first period after the implantation the stent surface is in direct contact with the blood and an acute thrombosis can occur which again occludes the vessel due to the now present foreign surface.

b.) The implantation of the stent generates vessel injuries, which induce inflammation reactions, which play an important role for the recovery process during the first seven days. The herein concurrent processes are among others connected with the release of growth factors, which initiate an increased proliferation of the smooth muscle cells which rapidly leads to a renewed occlusion of the vessel, because of uncontrolled growth.

c.) After a couple of weeks the stent starts to grow into the tissue of the blood vessel. This means that the stent is surrounded totally by smooth muscle cells and has no contact to the blood. This cicatrization can be too distinctive (neointima hyperplasia) and may lead to not only a coverage of the stent surface but to the occlusion of the total interior space of the stent.

It was tried vainly to solve the problem of restenosis by the coating of the stents with heparin (J. Whörle et al., European Heart Journal 2001, 22, 1808-1816). Heparin addresses as anti coagulant only the first mentioned cause and is moreover able to unfold its total effect only in solution. This first problem is meanwhile almost totally avoidable medicamentously by application of anti-coagulants. The second and third problem is intended now to be solved by inhibiting the growth of the smooth muscle cells locally on the stent. This is carried out by e.g. radioactive stents or stents which contain pharmaceutically active agents.

U.S. Pat. No. 5,891,108 discloses for example a hollow moulded stent, which can contain pharmaceutical active agents in its interior, that can be released throughout a various number of outlets in the stent. Whereas EP-A-1 127 582 describes a stent that shows ditches of 0.1-1 mm depth and 7-15 mm length on its surface which are suitable for the implementation of an active agent. These active agent reservoirs release similarly to the outlets in the hollow stent the contained pharmaceutically active agent in a punctually high concentration and over a relatively long period of time which however leads to the fact that the smooth muscle cells are not anymore or only very delayed capable of enclosing the stent. As a consequence the stent is much longer exposed to the blood, what leads again to increased vessel occlusions by thromboses (Liistro F., Colombo A., Late acute thrombosis after Paclitaxel eluting stent implantation. Heart 2001, 86, 262-264).

One approach to this problem is represented by the phosphorylcholine coating of biocompatibles (WO 0101957), as here phosphorylcholine, a component of the erythrocyte cell membrane, shall create a non thrombogeneous surface as a component of the coated non biodegradable polymer layer on the stent. Dependent of its molecular weight, thereby the active agent is absorbed by the polymer containing phosphorylcholine layer or adsorbed on the surface.

The stents according to invention are coated with a hemocompatible layer and feature one or more additional layers which at least comprise an antiproliferative and/or antiinflammatory and if needed an antithrombotic active agent.

The hemocompatible coating of a stent provides the required blood compatibility and the active agent (or active agent combination) which is distributed homogeneously over the total surface of the stent provides that the covering of the stent surface with cells especially smooth muscle and endothelial cells takes place in a controlled way. Thus no rapid population and overgrowth with cells takes place on the stent surface which could lead to a restenosis whereas the covering of the stent surface with cells is also not completely prevented by a high medicament concentration which involves the risk of thrombosis.

Thus the incorporation of active agents guarantees that the active agent or the active agent combination which is bound covalently and/or adhesively to the subjacent layer and/or implemented covalently and/or adhesively into the layer is released continuously and in small doses so that the population of the stent surface by cells is not inhibited however an overgrowth is prevented. This combination of both effects awards the ability to the inventive stent to grow rapidly into the vessel wall and reduces both the risk of restenosis and the risk of thrombosis. The release of one or more active agents spans over a period from 1 to 12 months, preferably 1 to 3 months after implantation.

Antiproliferative substances, antiphlogistic as well as antithrombotic compounds are used as active agents. Preferably cytostatics, macrolide antibiotics and/or statins are used as antiproliferative active agents. Applyable antiproliferative active agents are sirolimus (rapamycin), everolimus, pimecrolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, betulinic acid, camptothecin, lapachol, β-lapachone, podophyllotoxin, betulin, trofosfamide, podophyllic acid 2-ethylhydrazide, ifosfamide, chlorambucil, bendamustine, dacarbazine, busulfan, procarbazine, treosulfan, temozolomide, melanocyte-stimulating hormon (α-MSH), thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterin, ademetionine, myrtecaine, polidocanol, nonivamide, levomenthol, benzocaine, aescin, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, trastuzumab, exemestane, letrozole, goserelin, chephalomannin, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, selectin (cytokine antagonist), CETP inhibitor, cadherines, cytokinin inhibitors, COX-2 inhibitor, NFkB, angiopeptin, CIPROFLOXACIN (1-cyclopropyl-6-fluoro-4-oxo-7-(piperazin-1-yl)-quinoline-3-carboxylic acid), camptothecin, fluoroblastin, monoclonal antibodies, which inhibit the muscle cell proliferation, bFGF antagonists, probucol, prostaglandins, folic acid and derivatives, vitamines of the B-series, vitamine D-derivatives such as calcipotriol and tacalcitol, D24851, fumaric acid and its derivatives such as dimethylfumarate, IL-1β inhibitor, colchicine, NO donors such as pentaerythritol tetranitrate and syndnoeimines, S-nitrosoderivatives, tamoxifen, staurosporin, β-estradiol, α-estradiol, estrone, estriol, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, paclitaxel and derivatives thereof (6-α-hydroxy-paclitaxel, baccatin, and others), synthetically produced as well as from native sources obtained macrocyclic oligomers of carbon suboxide (MCS) and derivatives thereof, molgramostim (rhuGM-CSF), peginterferon α-2b, lenograstim (r-HuG-CSF), filgrastim, macrogol, dacarbazine, letrozol, goserelin, chephalomannin, trastuzumab, exemestan, basiliximab, daclizumab, ellipticine, D-24851 (Calbiochem), COLCEMID ((S)-6,7-Dihydro-1,2,3,10-tetramethoxy-7-(methylamino)benzo[a]heptalen-9(5H)-on), cytochalasin A-E, indanocine, nocodazole, S 100 protein, PI-88, melanocyte stimulating hormon (α-MSH), bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, interleucine-1β inhibitors, antisense oligonucleotides, VEGF inhibitors, called IGF-1.

From the group of antibiotics furthermore cefadroxil, cefazolin, cefaclor, cefotixin, tobramycin, gentamycin are used. Positive influence on the postoperative phase have also the penicillins such as dicloxacillin, oxacillin, sulfonamides, metronidazol, antithrombotics such as argatroban, aspirin, abciximab, synthetic antithrombin, bivalirudin, COUMADIN (warfarin sodium), dermicidin, enoxaparin, hemoparin, tissue plasminogen activator, GpIIb/IIIa platelet membrane receptor, factor $X_a$ inhibitor, activated protein C, dermicidin, antibodies, heparin, hirudin, r-hirudin, PPACK, protamin, prourokinase, streptokinase, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, caspase inhibitors, apoptosis inhibitors, apoptosis regulators such as p65 NF-kB and Bc1-xL antisense oligonucleotides and prostacyclin, vapiprost, α, β and γ interferon, histamine antagonists, serotonin blockers, halofuginone, nifedipine, tocopherol, tranirast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, procainamid, retinoic acid, quinidine, disopyramide, flecamide, propafenone, sotalol, amidorone. Further active agents are steroids (hydrocortisone, betamethasone, dexamethasone), non-steroidal substances (NSAIDS) such as fenoprofen, ibuprofen, indomethacin, naproxen, phenylbutazone and others. Antiviral agents such as acyclovir, ganciclovir and zidovudine are also applyable. Different antimycotics are used in this area. Examples are clotrimazole, flucytosine, griseofulvin, ketoconazole, miconazole, nystatin, terbinafine. Antiprozoal agents such as chloroquine, mefloquine, quinine are effective active agents in equal measure, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3, tubeimoside, bruceanol A, B, C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-α-senecioyloxychaparrin, 1,11-dimethoxycanthin-6-one, 1-hydroxy-11-methoxycanthin-6-one, scopoletin, taxamairin A and B, regenilol, triptolide, moreover cymarin, apocymarin, aristolochic acid, anopterin, hydroxyanopterin, anemonin, protoanemonin, BERBERINE (5,6-dihydro-9,10-dimethoxybenzo[g]-1,3-benzodioxolo[5,6-a] quinolizinium), cheliburin chloride, cictoxin, sinococuline, bombrestatin A and B, cudraisoflavone A, curcumin, dihydronitidine, nitidine chloride, 12-β-hydroxypregnadien-3, 20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, vismione A and B, further natural terpenoids such as hippocaesculin, 14-dehydroagrostistachin, agroskerin, agrostistachin, 17-hydroxyagrostistachin, ovatodiolids, 4,7-oxycycloanisomelic acid, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin.

The active agents are used separately or combined in the same or a different concentration. Especially preferred are active agents which feature also immunosuppressive properties besides their antiproliferative effect. Suchlike active agents are erythromycin, midecamycin, tacrolimus, sirolimus, paclitaxel and josamycin. Furthermore preferred is a combination of several antiproliferatively acting substances or of antiproliferative active agents with immunosuppressive active agents.

Preferred for the present invention are tacrolimus, pimecrolimus, PI88, thymosin α-1, PETN (pentaerythritol tetranitrate), baccatin and its derivatives, docetaxel, colchicin, paclitaxel and its derivatives, trapidil, α- and β-estradiol, dermicidin, simvastatine, macrocyclic suboxide (MCS) and its derivatives, sirolimus, tyrphostines, D24851, colchicin, fumaric acid and fumaric acid esters, activated protein C (aPC), interleucine-1β inhibitors and melanocyte-stimulating hormone (α-MSH) and tialin (2-methylthiazolidine-2,4-dicarboxylic acid) as well as tialin-Na (sodium salt of tialin).

The active agent is preferably contained in a pharmaceutical active concentration from 0.001-10 mg per $cm^2$ stent surface and per active agent layer or active agent containing layer. Additional active agents can be contained in a similar concentration in the same or in other layers.

The medical devices coated according to invention, especially the stents coated according to invention, can release the active agent or the active agents continuously and controlled and are suitable for the prevention or reduction of restenosis (see FIG. 6).

The hemocompatible layer which covers directly the stent preferably comprises heparin of native origin as well as synthetically obtained derivatives with different sulphation coefficients (sulphation degrees) and acylation coefficients (acylation degrees) in the molecular weight range of the pentasaccharide which is responsible for the antithrombotic activity up to the standard molecular weight of the purchasable heparin, as well as heparan sulphates and derivatives thereof, oligo- and polysaccharides of the erythrocyte glycocalix, which imitate in a perfect way the athrombogeneous surface of the erythrocytes, since contrary to phosphorylcholine, here the actual contact between blood and erythrocyte surface takes place, completely desulphated and N-reacetylated heparin, desulphated and N-reacetylated heparin, N-carboxymethylated and/or partially N-acetylated chitosan, chitosan and/or mixtures of these substances. These stents with a hemocompatible coating are prepared by providing conventional normally non coated stents and by preferably covalent deposition of a hemocompatible layer which permanently masks the surface of the implant after the release of the active agent and thus, after the decay of the active agent's influence and the degradation of the matrix.

The conventional stents which can be coated according to the inventive methods, consist of stainless steel, nitinol or other metals and alloys or of synthetic polymers.

Another preferred embodiment of the stents according to invention shows a coating which consists of at least two layers. Multiple layer systems are used as well. In such multiple layer systems the layer which is directly deposited on the stent is labelled first layer. Labelled second layer is that layer which is deposited on the first layer, etc.

According to the two layer design the first layer consists of a hemocompatible layer which is substantially covered completely by a biodegradable layer which comprises at least an antiproliferative, antiphlogistic and/or antithrombotic active agent bound covalently and/or adhesively. Also applied are active agent combinations which mutually facilitate and replenish themselves.

As biodegradable substances for the external layer can be used: polyvalerolactones, poly-ε-decalactones, polylactonic acid, polyglycolic acid, polylactides, polyglycolides, copolymers of the polylactides and polyglycolides, poly-ε-caprolactone, polyhydroxybutanoic acid, polyhydroxybutyrates, polyhydroxyvalerates, polyhydroxybutyrate-co-valerates, poly(1,4-dioxane-2,3-diones), poly(1,3-dioxane-2-ones), poly-p-dioxanones, polyanhydrides such as polymaleic anhydrides, polyhydroxymethacrylates, fibrin, polycyanoacrylates, polycaprolactonedimethylacrylates, poly-b-maleic acid, polycaprolactonebutyl-acrylates, multiblock polymers such as from oligocaprolactonedioles and oligodioxanonedioles, polyether ester multiblock polymers such as PEG and polybutyleneterephtalate, polypivotolactones, polyglycolic acid trimethyl-carbonates, polycaprolactoneglycolides, poly-g-ethylglutamate, poly(DTH-iminocarbonate), poly(DTE-co-DT-carbonate), poly(bisphenol-A-iminocarbonate), polyorthoesters, polyglycolic acid trimethylcarbonates, polytrimethylcarbonates, polyiminocarbonates, poly(N-vinyl)-pyrrolidone, polyvinylalcoholes, polyesteramides, glycolated polyesters, polyphosphoesters, polyphosphazenes, poly[p-carboxyphenoxy)propane], polyhydroxypentanoic acid, polyanhydrides, polyethyleneoxidepropyleneoxide, soft polyurethanes, polyurethanes with amino acid residues in the backbone, polyether esters such as polyethyleneoxide, polyalkeneoxalates, polyorthoesters as well as copolymers thereof, lipids, carrageenanes, fibrinogen, starch, collagen, protein based polymers, polyamino acids, synthetic polyamino acids, zein, modified zein, polyhydroxy-alkanoates, pectic acid, actinic acid, modified and non modified fibrin and casein, carboxymethylsulphate, albumin, moreover hyaluronic acid, heparan sulphate, heparin, chondroitinesulphate, dextran, b-cyclodextrines, copolymers with PEG and polypropyleneglycol, gummi arabicum, guar, gelatine, collagen, collagen-N-hydroxysuccinimide, lipids, phospholipids, modifications and copolymers and/or mixtures of the afore mentioned substances.

The layer and layers respectively which contain the active agent is slowly degradated by components of the blood such that the active agent is released of the external layer according to the degradation velocity or resolves itself from the matrix according to its elution behavior. The first hemocompatible layer guarantees the required blood compatibility of the stent once the biodegradable layer is degraded. This biological degradation of the external layer and the corresponding release of the active agent reduces strongly an ongrowth of cells only for a certain period of time and an aimed controlled adhesion is enabled where the external layer has been already widely degradated. The biological degradation of the external layer spans advantageously from 1 to 36 months, preferably from 1 to 6 months, especially preferred from 1 to 2 months. It was shown that suchlike stents prevent or at least very strongly reduce restenosis. In this period of time the important healing processes take place. Finally the hemocompatible layer remains as athrombogeneous surface and masks the foreign surface in such a way that no life-threatening reaction can occur anymore.

The amounts of polymer deposited on the surfaces of the medical devices, preferably stents, are between 0.01 mg to 3 mg/layer, preferred between 0.20 mg to 1 mg/layer and especially preferred between 0.2 mg to 0.5 mg/layer.

Such like stents are preparable via a method for the hemocompatible coating of stents the basis of which is formed by the following principle:

a) providing a non coated stent,
b) deposition of a preferred covalently bound hemocompatible layer,
c) diffusion of active agent into the hemocompatible layer, or
c') substantially complete coating of the hemocompatible layer via dipping or spraying method with at least one active agent, or
c") substantially complete coating and/or incomplete coating of the hemocompatible layer via dipping or spraying method with at least one biodegradable and/or biostable layer which comprises at least one active agent and/or represents the active agent itself.

The principle of coating offers a big range of variation concerning the contrived requirements for the active agent and is separable into different coating types, which can be combined also among themselves.

Coating Principle I:
a) providing a non coated stent,
b) deposition of a hemocompatible layer,
c) deposition of an active agent or an active agent combination on the hemocompatible layer without a matrix,
d) deposition of an active agent or an active agent combination on the hemocompatible layer without a matrix and substantially complete and/or incomplete coating of the layers with a biodegradable and/or biostable material for diffusion control.

Coating Principle II:
a) providing a non coated stent,
b) deposition of a hemocompatible layer,
c) substantially complete coating and/or incomplete coating of the hemocompatible layer with at least one biodegradable and/or biostable layer which comprises at least one active agent bound covalently and/or adhesively to the hemocompatible layer,
d) substantially complete coating of the hemocompatible layer with at least one biodegradable and/or biostable layer which comprises at least one active agent bound covalently and/or adhesively to the matrix and another biodegradable and/or biostable layer without an active agent as diffusion barrier which covers the subjacent layer completely and/or partially.

Coating Principle III:
a) providing a non coated stent,
b) deposition of a hemocompatible layer,
c) substantially complete coating of the hemocompatible layer with at least one biodegradable and/or biostable layer which comprises at least one active agent bound covalently and/or adhesively,
d) deposition of an active agent or an active agent combination bound covalently and/or adhesively to the subjacent layer,
e) substantially complete coating of the hemocompatible layer with at least one biodegradable and/or biostable layer which comprises at least one active agent bound covalently and/or adhesively, deposition of an active agent or an active agent combination and another biodegradable and/or biostable layer without an active agent as diffusion barrier which covers the subjacent layer completely and/or partially.

Coating Principle IV:
a) providing a non coated stent,
b) deposition of a hemocompatible layer,
c) substantially complete and/or incomplete coating of the hemocompatible layer with at least two biodegradable and/or biostable layers which comprise covalently and/or adhesively at least one active agent in a different concentration per layer,
d) substantially complete and/or incomplete coating of the hemocompatible layer with at least two biodegradable and/or biostable layers which comprise at least one active agent bound covalently and/or adhesively in a different concentration per layer and at least another biodegradable and/or biostable layer without an active agent as diffusion barrier which covers the subjacent layer completely and/or partially,
e) substantially complete and/or incomplete coating of the hemocompatible layer with at least one biodegradable and/or biostable layer which comprises at least one active agent and/or at least another active agent of the same group or from another group of complementary properties in the same or different concentrations in a covalent and/or adhesive form,
f) substantially complete and/or incomplete coating of the hemocompatible layer with at least two biodegradable and/or biostable layers which comprise at least one active agent and/or at least another active agent of the same group or from another group of complementary properties in the same or different concentrations and at least another biodegradable and/or biostable layer without an active agent as diffusion barrier which covers the subjacent layer completely and/or partially,
g) substantially complete coating of the hemocompatible layer with at least two biodegradable and/or biostable layers which comprise covalently and/or adhesively at least one active agent in the same and/or different concentrations and another biodegradable and/or biostable layer without an active agent as diffusion barrier which covers the subjcent layer completely or also just partially and whereas that layer is covered by an active agent layer which consists of at least one active agent bound covalently to the subjacent matrix and/or adhesively without a support material.

Another advantageous embodiment is represented by a stent with an at least three layered coating, whereas the first layer covers the surface of the stent with the hemocompatible layer, the second layer contains the active agent and is not biodegradable and is covered by a third hemocompatible layer. The external layer provides the stent herein the necessary blood compatibility and the second layer serves as an active agent reservoir. The active agent which is if needed covalently bound to the matrix via a hydrolysis-weak bonding and/or added in a solvent dissolved matrix which is required for the coating method, is thus released from the second layer continuously and in small concentrations and diffuses uninhibited through the external hemocompatible layer. This layer assembly also yields the result that the population of the stent surface with cells is not prevented but is reduced to an ideal degree. The first layer offers a risk minimization for eventually occurring damages of the coated stent surface during the implantation e.g. by abrasions through the present plaque or during the prearrangement e.g. during the crimping. A second security guarantee results from the fact that even a bio-stable polymer is degraded in the body over a more or less long period of time which at least partially uncovers the stent surface. Combinations especially with biodegradable material as described in the coating principles are possible, too.

Suchlike stents can be prepared by providing a conventional stent, depositing a hemocompatible first layer on its surface, depositing a non biodegradable layer which at least comprises one active agent as well as combinations with other active agents from other groups bound covalently and/or adhesively and coating of this layer substantially completely with another hemocompatible layer.

Substances which come into question for the biostable layer are all of the consistent materials used in medical science. Thereto are accounted: polyacrylic acid and polyacrylates such as polymethylmethacrylate, polybutyl methacrylate, polyacrylamide, polyacrylonitriles, polyamides, polyetheramides, polyethylenamine, polyimides, polycarbonates, polycarbourethanes, polyvinylketones, polyvinylhalogenides, polyvinylidenhalogenides, polyvinyl ethers, polyvinylaromates, polyvinyl esters, polyvinylpyrrolidones, polyoxymethylenes, polyethylene, polypropylene, polytetrafluoroethylene, polyurethanes, polyolefin elastomers, polyisobutylenes, EPDM gums, fluorosilicones, carboxymethyl chitosan, polyethylenterephthalate, polyvalerates, carboxymethylcellulose, cellulose, rayon, rayon triacetates, cellulose nitrates, cellulose acetates, hydroxyethylcellulose, cellulosebutyrates, celluloseacetatebutyrates, ethylvinylacetate copolymers, polysulphones, epoxy resins, ABS resins, EPDM gums, silicones such as polysiloxanes, polyvinylhalogenes and copolymers, cellulose ethers, cellulose triacetates, chitosan and copolymers and/or mixtures of these afore-mentioned substances.

In case of multi layer systems the newly deposited layer covers the subjacent layer substantially completely. The term "substantially" means in this context, that at least the stent surface, which comes into contact with the vessel wall, is covered completely resp. at least 90%, preferred 95% and especially preferred at least 98% of the stent surface are covered.

The stents according to invention solve both the problem of acute thrombosis and the problem of neointima hyperplasia after a stent implantation. In addition the stents according to invention are well suitable due to their coating whether as single layer or as multi layer system especially for the continuous release of one or more antiproliferative and/or immunosuppressive active agents. Due to this feature of aimed continuous active agent release in a required amount the coated stents according to invention prevent almost completely the danger of restenosis.

In addition, according to the described process, any plastic surfaces can be coated with a hemocompatible layer of the oligosaccharides and/or polysaccharides. As plastics, synthetic polymers as well as biopolymers are suitable, comprising, for example, the monomers ethene, vinyl acetate, methacrylic acid, vinylcarbazole, trifluoro ethylene, propene, butene, methylpentene, isobutene, styrene, chlorostyrene, aminostyrene, acrylonitrile, butadiene, acrylic ester, divinylbenzene, isoprene, vinyl chloride, vinyl alcohol, vinylpyridine, vinylpyrrolidone, tetrafluoroethylene, trifluorochloroethene, vinyl fluoride, hexafluoroisobutene, acrylic acid, acrolein, acrylamide, methacrylamide, maleic acid, hydroxymethyl methacrylic acid, methyl methacrylic acid, maleic acid anhydride, methacrylic acid anhydride, methacrylonitrile, fluorstyrene, fluoranilide, 3,4-isothiocyanatostyrene, allyl alcohol, sulfonic acid, methallylsulfonic acid, diallyl phthalic acid, cyanoacrylic acid, dimethylaminoethylmethacrylic acid, lauryl methacrylic acid, acetaminophenylethoxymethacrylic acid, glycol dimethacrylic acid, 2-hydroxyethyl methacrylic acid, formaldehyde, fluoral, chloral, ethylene oxide, tetrahydrofuran, propylene oxide, allyl glycidyl ether, epichlorohydrin, glycerin, trimethylpropane, pentaerythrite, sorbite, phthalic acid, succinic acid, fumaric acid, adipinic acid, thiophene, ethyleneimine, hexamethylene adipamide, hexamethylene sebacamide, hexamethylene dodecane diamide, aminobenzamide, phenylene diamine, amide hydrazides, dimethyl piperazine, benzimidazole, tetraminobenzene, pyrones, ε-caprolactam, isophthalic acid, glutaminic acid, leucine, phenyl alanine, valine, lysine, urea, diisocyanate, thiourea and others or mixtures of the above mentioned monomers. Furthermore, the following polymers can be considered: silicones, cellulose and cellulose derivatives, oils, polycarbonates, polyurethane, agarose, polysaccharides, dextranes, starch, chitin, glycosamino glycans, gelatin, collagen I-XII and other proteins.

EXAMPLES

Example 1

Preparation of Desulphated Reacetylated Heparin 100 ml of amberlite IR-122 cation exchange resin were filled into a column having a diameter of 2 cm, transformed into the $H^+$-form with 400 ml 3M HCl and washed with distilled water until the eluate was free from chloride and pH neutral. 1 g of sodium heparin was dissolved in 10 ml of water, put onto the cation-exchange column and eluted with 400 ml of water. The eluate was allowed to drop into a receiver with 0.7 g of pyridine and subsequently titrated with pyridine to pH 6 and freeze-dried.

0.9 g of heparin pyridinium salt were added to 90 ml of a 6/3/1 mixture of DMSO/1,4-dioxane/methanol (v/v/v) in a round bottomed flask with reflux cooler and heated to 90° C. for 24 hours. Then, 823 mg of pyridinium chloride were added and heating to 90° C. was effected for further 70 hours. Subsequently, dilution was carried out with 100 ml of water, and titration to pH 9 with dilute soda lye was effected. The desulphated heparin was dialyzed against water and freeze-dried.

100 mg of the desulphated heparin were dissolved in 10 ml of water, cooled to 0° C. and mixed with 1.5 ml of methanol under stirring. To the solution, 4 ml of Dowex 1×4 anion-exchange resin in the OH⁻-form and subsequently 150 µl of acetic acid anhydride were added and stirred for 2 hours at 4° C. After that, the resin is filtrated, and the solution is dialyzed against water and freeze-dried.

Example 2

N-carboxymethylated, partially N-acetylated chitosan

In 150 ml 0.1 N HCl, 2 g of chitosan were dissolved and boiled under nitrogen for 24 hours under reflux. After cooling to room temperature, the pH of the solution was adjusted to 5.8 with 2 N NaOH. The solution was dialyzed against demineralized water and freeze-dried.

1 g of the chitosan partially hydrolyzed this way was dissolved in 100 ml of a 1% acetic acid. After adding 100 ml of methanol, 605 µl of acetic acid anhydride dissolved in 30 ml of methanol were added and stirred for 40 minutes at room temperature. The product was precipitated by pouring into a mixture of 140 ml of methanol and 60 ml of a 25% $NH_3$ solution. It was filtrated, washed with methanol and diethyl ether and dried under vacuum over night.

1 g of the partially hydrolyzed and partially N-acetylated chitosan was suspended in 50 ml of water. After adding 0.57 g of glyoxylic acid monohydrate, the chitosan derivative dissolved within the next 45 minutes. The pH value of the solution was adjusted to 12 with 2 N NaOH. A solution of 0.4 g of sodium cyanoboron hydride in as few water as possible was added and stirred for 45 minutes. The product was precipitated in 400 ml of ethanol, filtrated, washed with ethanol and dried in vacuum over night.

Example 3

Synthesis of desulphated N-propionylated heparin 100 ml amberlite IR-122 cation exchange resin were added into a column of 2 cm diameter, with 400 ml 3M HCl in the H'-form converted and rinsed with distilled water, until the eluate was free of chloride and pH neutral. 1 g sodium-heparin was dissolved in 10 ml water, added onto the cation exchange column and eluted with 400 ml of water. The eluate was added dropvise into a receiver with 0.7 g pyridine and afterwards titrated with pyridine to pH 6 and freeze-dried.

0.9 g heparin-pyridinium-salt were added in a round flask with a reflux condenser with 90 ml of a 6/3/1 mixture of DMSO/1,4-dioxan/methanol (v/v/v) and heated for 24 hours to 90° C. Then 823 mg pyridiniumchloride were added and heated additional 70 hours to 90° C. Afterwards it was diluted with 100 ml of water and titrated with dilute sodium hydroxide to pH 9. The desulphated heparin was dialyzed contra water and freeze-dried.

100 mg of the desulphated heparin were solved in 10 ml of water, cooled to 0° C. and added with 1.5 ml methanol under stirring. To this solution were added 4 ml dowex 1×4 anion exchange resin in the OH⁻-form and afterwards 192 µl of propionic anhydride and stirred for 2 hours at 4° C. Then the resin was removed by filtration and the solution was dialyzed contra water and freeze-dried.

Example 4

N-carboxymethylated, partially N-propionylated chitosan

In 150 ml 0.1 N HCl, 2 g of chitosan were dissolved and boiled under nitrogen for 24 hours under reflux. After cooling to room temperature, the pH of the solution was adjusted to 5.8 with 2 N NaOH. The solution was dialyzed against demineralized water and freeze-dried. 1 g of the chitosan partially hydrolyzed this way was dissolved in 100 ml of a 1% acetic acid. After adding 100 ml of methanol, 772 µA of propionic acid anhydride dissolved in 30 ml of methanol were added and stirred for 40 minutes at room temperature. The product was precipitated by pouring into a mixture of 140 ml of methanol and 60 ml of a 25% $NH_3$ solution. It was filtrated, washed with methanol and diethyl ether and dried under vacuum over night.

1 g of the partially hydrolyzed and partially N-acetylated chitosan was suspended in 50 ml of water. After adding 0.57 g of glyoxylic acid monohydrate, the chitosan derivative dissolved within the next 45 minutes. The pH value of the solution was adjusted to 12 with 2 N NaOH. A solution of 0.4 g of sodium cyanoboron hydride in as few water as possible was added and stirred for 45 minutes. The product was precipitated in 400 ml of ethanol, filtrated, washed with ethanol and dried in vacuum over night.

Example 5

Hemocompatibility measurements of compounds according to the general formula Ia and Ib by ISO 10933-4 (in vitro measurements)

For the measurement of the hemocompatibility of the compounds according to formulas Ia and Ib cellulose membranes, silicon tubes and stainless steel stents were covalently coated with a compound according to formula Ia and Ib and tested contra heparin as well as contra the corresponding, in the single tests utilised uncoated material surfaces.

5.1. Cellulose Membranes (Cuprophan) Coated with Desulphated, Reacetylated Heparin (Ac-Heparin)

For the examination of the coagulatory physiologic interactions between citrated whole blood and the Ac-heparin-resp. heparin-coated cuprophan membranes the open perfusion system of the Sakariassen-modified Baumgartner-chamber is used [Sakariassen K. S. et al.; *J. Lab. Clin. Med.* 102:522-535 (1983)]. The chamber is composed of four building parts plus conical nipples and threaded joints and is manufactured of polymethylmethacrylate and allows the parallel investigation of two modified membranes, so that in every run already a statistic coverage is included. The construction of this chamber permits quasi laminar perfusion conditions.

After 5 minutes of perfusion at 37° C. the membranes are extracted and after fixation of the adherent platelets the platelet occupancy is measured. The respective results are set into relation to the highly thrombogeneous subendothelial matrix as negative standard with a 100% platelet occupancy. The adhesion of the platelets takes place secondary before the formation of the plasma protein layer on the foreign material. The plasma protein fibrinogen acts as cofactor of the platelet aggregation. The such induced activation of the platelets results in the bonding of several coagulation associated plasma proteins, such as vitronectin, fibronectin and von Willebrand-factor on the platelet surface. By their influence finally the irreversible aggregation of the platelets occurs. The platelet occupancy presents because of the described interactions an accepted quantum for the thrombogenity of surfaces in case of the foreign surface contact of blood. From this fact the consequence arises: the lower the platelet occupancy is on the perfunded surface the higher is the hemocompatibility of the examined surface to be judged.

The results of the examined heparin-coated and Ac-heparin-coated membranes show clearly the improvement of the hemocompatibility of the foreign surface through the coating with Ac-heparin. Heparin-coated membranes show a 45-65% platelet occupancy, whilst Ac-heparin-coated surfaces show values from 0-5% (reference to subendothelial matrix with 100% platelet occupancy).

The adhesion of the platelets on the Ac-heparinated surface is extremely aggravated due to the absent, for the activation of platelets essential plasma proteins. Unlike to this the heparin-coated surface with the immediately incipient plasma protein adsorption offers optimal preconditions for activation, deposition and aggregation of platelets, and ultimately the blood reacts with the corresponding defense mechanisms to the inserted foreign surface by activation of the coagulation cascade. Ac-heparin fulfills by far superior than heparin the requirements to the hemocompatibility of the foreign surface.

The interaction of plasma protein adsorption and platelet occupancy as direct quantum for the thrombogenity of a surface, in dependence of the to the blood offered coating, is made clear especially well by this in-vitro test. Thus the utilisation of covalently bound heparin as antithrombotic operant surface is only strongly limited or not possible at all. The interactions of immobilised heparin with blood revert themselves here into the undesired opposite—the heparin-coated surface gets thrombogeneous.

Obviously the outstanding importance of heparin as an antithrombotic is not transferable to covalently immobilised heparin. In the systemic application in dissolved form it can fully unfold its properties. But if heparin is not covalently immobilised, its antithrombotic properties, if at all, is only short-lived. Different is the Ac-heparin ("No-affinity"-heparin), that due to the desulphation and N-reacetylation in fact totally loses the active antithrombotic properties of the initial molecule, but acquires in return distinctive athrombogeneous properties, that are demonstrably founded in the passivity versus antithrombin III and the missing affinity towards coagulation initiating processes and remain after covalent bonding.

Thereby Ac-heparin and thus the compounds of the general formulas Ia and Ib in total are optimally suitable for the camouflage of foreign surfaces in contact with the coagulation system.

5.2. Immobilization on Silicone

Through a 1 m long silicon tube with 3 mm inside diameter 100 ml of a mixture of ethanol/water 1/1 (v/v) was pumped in a circular motion for 30 minutes at 40° C. Then 2 ml 3-(triethoxysilyl)-propylamine were added and pumped in a circular motion for additional 15 hours at 40° C. Afterwards it was rinsed in each case for 2 hours with 100 ml ethanol/water and 100 ml water.

3 mg of the deacetylated and reacetylated heparin (Ac-heparin) were dissolved at 4° C. in 30 ml 0.1 M MES buffer pH 4.75 and mixed with 30 mg CME-CDI (N-cyclohexyl-N'-(2-morpholinoethyl)carbodiimidemethyl-p-toluenesulphonate). This solution was pumped in a circular motion for 15 hours at 4° C. through the tube. Afterwards it was rinsed with water, 4 M NaCl solution and water in each case for 2 hours.

5.3. Determination of the Platelet Number (EN30993-4)

In a 1 m long silicone tube with 3 mm inside diameter two 2 cm long formfitting glass tubes were placed. Then the tube was closed with a shrinkable tubing to a circle and filled under exclusion of air via syringes with a 0.154 M NaCl solution. In doing so one syringe was used to fill in the solution and the other syringe was used to remove the air. The solution was exchanged under exclusion of air (bleb-free) with the two syringes against citrated whole blood of a healthy test person. Then the recess holes of the syringes were closed by pushing the glass tubes over them and the tube was clamp taut into a dialysis pump. The blood was pumped for 10 minutes with a flow rate of 150 ml/min. The platelet content of the blood was measured before and after the perfusion with a Coulter counter. For uncoated silicone tubes the platelet loss was of 10%. In contrast to it the loss was in silicon tubes, which were coated according to example 5.2, in average at 0% (number of experiments: n=3).

Also in this dynamic test system it is shown, that the activation of platelets on an Ac-heparin coated surface is reduced. Simultaneously it can be recorded, that the immobilisation of heparin executes a negative effect on the hemocompatibility of the utilised surface. Against it Ac-heparin shows, in accordance to its passive nature, no effects in contact with the platelets.

5.4. Whole Blood Experiments on 316 LVM Stainless Steel Coronary Stents

In line with the biocompatibility experiments 31 mm long 316 LVM stainless steel stents were covalently coated with Ac-heparin. In case of a total surface of 2 $cm^2$ and a occupancy coefficient of about 20 $pm/cm^2$ stent surface the charging of such a stent is about 0.35 µg Ac-heparin. As comparison: in case of thrombosis prophylaxis the usual daily application rate of heparin is in contrast 20-30 mg and thus would correspond to the at least 60.000 times the value.

These experiments were carried out at the Intitute of Physiology at the RWTH Aachen with the established hemodynamic Chandler loop-system [A. Henseler, B. Oedekoven, C. Andersson, K. Mottaghy; KARDIOTECHNIK 3 (1999)]. Coated and uncoated stents were expanded and tested in PVC tubes (medical grade PVC) with 600 mm length and 4 mm inside diameter. The results of these experiments confirm the according to the silicone tubes discussed experiments. The initially to the stent attributed platelet loss in the perfusate of 50% is reduced by the refinement of the stent surface with Ac-heparin by more than 80%.

The influence of in the tube expanded, surface modified coronary stents to the platelet loss is evaluated in further Chandler tests during a 45 minute whole blood perfusion. For this primarily the stent-free PVC tube is analysed, the outcome of this is the zero value. The empty tube shows an average platelet loss of 27.4% regarding to the donor blood at a standard aberration of solely 3.6%. This base value underlied different surface modified stents are expanded in the PVC tubes and are analysed under analogous conditions on the by them caused platelet loss. It occurs also in this case, that the stent covered surface, which solely accounts for about 0.84% of the total test surface, causes a significant and reproducable effect on the platelet content. According to the empty tube (base value) the analysis of the polished, chemically not surface coated stent yields an additional average platelet loss of 22.7%. Therewith causes this compared to the PVC empty tube less than 1% measurable foreign surface an approximately comparable platelet loss. A direct result is that the medicinal stainless steel 316 LVM used as stent material induces an about 100 times stronger platelet damage compared to a medical grade PVC surface, although this test surface only accounts for 0.84% of the total surface.

Figure 4:
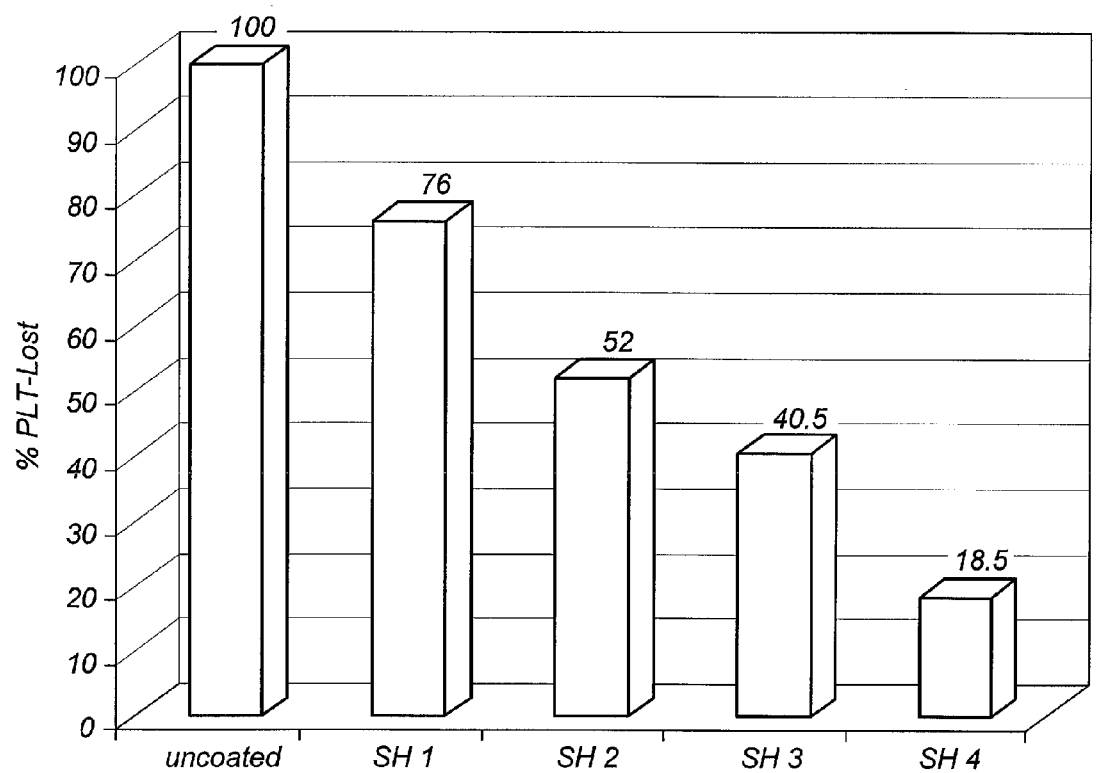
FIG. 4 shows the influence of an into a PVC-tube expanded, surface modified stainless steel coronary stent on the platelet loss (PLT-loss). An uncoated stainless steel coronary stent was measured (uncoated) as reference. As zero value the level of the platelet loss in case of the PVC-tube without stainless steel coronary stent was set.

The analysed surface coatings on the stainless steel coronary stents show to be able to reduce very clearly the enormous dimension of the stent induced platelet damage (see FIG. 4). As most effective proved with 81.5% the Ac-heparin (SH4).

If the effects of the Ac-heparin-coated stents on the platelet loss are considered, then good congruent values result. The correlation of the platelet loss in the perfusate resp. the adhesion of the platelets to the offered surfaces show the reliability of the measurements.

5.4.1 Covalent Hemocompatible Coating of Stents

Not expanded stents of medicinal stainless steel LVM 316 were degreased in the ultrasonic bath for 15 minutes with acetone and ethanol and dried at 100° C. in the drying closet. Then they were dipped for 5 minutes into a 2% solution of 3_aminopropyltriethoxysilane in a mixture of ethanol/water (50/50: (v/v)) and then dried for 5 minutes at 100° C. Afterwards the stents were washed with demineralised water over night.

3 mg desulphated and reacetylated heparin were dissolved at 4° C. in 30 ml 0.1 M MES-buffer (2-(N-morpholino) ethanesulphonic acid) pH 4.75 and mixed with 30 mg N-cyclohexyl-N'-(2-morpholinoethyl)carbodiimide-methyl-p-toluenesulphonate. In this solution 10 stents were stirred for 15 hours at 4° C. Then they were rinsed with water, 4 M NaCl solution and water in each case for 2 hours.

5.4.2 Determination of the Glucosamine Content of the Coated Stents by HPLC

Hydrolysis: the coated stents are given in small hydrolysis tubes and are abandoned with 3 ml 3 M HCl for exactly one minute at room temperature. The metal probes are removed and the tubes are incubated after sealing for 16 hours in the drying closet at 100° C. Then they are allowed to cool down, evaporated three times until dryness and taken up in 1 ml degassed and filtered water and measured contra an also hydrolysated standard in the HPLC:

| stent | sample area | desulphat. + reacet. heparin [g/sample] | area [cm$^2$] | desulphat. + reacet. heparin [g/cm$^2$] | desulphat. + reacet. heparin [pmol/cm$^2$] |
|---|---|---|---|---|---|
| 1 | 129.021 | 2.70647E−07 | 0.74 | 3.65739E−07 | 41.92 |
| 2 | 125.615 | 2.63502E−07 | 0.74 | 3.56084E−07 | 40.82 |
| 3 | 98.244 | 1.93072E−07 | 0.74 | 2.60908E−07 | 29.91 |
| 4 | 105.455 | 2.07243E−07 | 0.74 | 2.80058E−07 | 32.10 |
| 5 | 119.061 | 2.33982E−07 | 0.74 | 3.16192E−07 | 36.24 |
| 6 | 129.202 | 2.53911E−07 | 0.74 | 3.43124E−07 | 39.33 |
| 7 | 125.766 | 2.53957E−07 | 0.74 | 3.43185E−07 | 39.34 |

Example 6

In Vivo Examination of Coated Coronary Stents (FIG. 5)

6.1. In Vivo Examinations of Coronary Stents Coated with Ac-Heparin

Due to the data on hemocompatibility, which Ac-heparin yielded in the in-vitro experiments, the suitability of the Ac-heparin surface as athrombogeneous coating of metal stents was discussed in vivo (animal experiment). The target of the experiments was primarily to evaluate the influence of the Ac-heparin coating on the stent induced vessel reaction. Besides the registration of possible thrombotic events the relevant parameters for restenotic processes like neointima area, vessel lumen and stenosis degree were recorded.

The animal experiments were carried out at the Inselspital Bern (Switzerland) under the direction of Prof. Hess an accredited cardiologist. For the examinations 6-9 month old domestic porks were used, one for the validation of stents for a long time established and approved animal model.

As expected in these experiments neither acute, subacute nor late acute thrombotic events were registered, what may be assessed as proof for the athrombogeneous properties of Ac-heparin.

After four weeks the animals were dispatched (euthanized), the stented coronary artery segments extracted and histomorphometrically analysed.

Indications to a possible acute or subchronic toxicity, allergisation reactions or ulterior irritations as consequence of the implantation of Ac-heparin coated stents are not observed during the complete experimental phase, especially in the histologic examination. During the stent implantation as well as the follow-up coronary-angiographic data sets were ascertained, which permit an interpretation with regard to the vessel reaction to the stent implantation.

The difference between the uncoated control stent and the Ac-heparin coated stent is unambiguous. The generation of a distinct neointima layer is in case of the uncoated control stent very well observable. Already after four weeks the proliferation promotional effect of the uncoated stent surface on the surrounding tissue occurs in such a degree, that ultimately the danger of the vessel occlusion in the stent area is given.

Contrary in case of the Ac-heparin coated stents a clearly thinner neointima layer is observed, which argues for a well modulated ingrowth of the stent under maintenance of a wide, free vessel lumen.

The detailed histomorphometric and coronary angiographic data substantiate this conclusion, as it can be observed congruently, that via the Ac-heparin coating (SH4) the neointima hyperplasia ("restenosis") was repressed by about 17-20% in comparison to the uncoated control stent. This result is unexpected and remarkably at the same time. Surely it is not demanded of an athrombogeneous surface to have an influence also on processes that lead to a neointima hyperplasia, i.e. to prevent restenoses, in addition to the preposition of hemocompatible characteristics.

On the one hand with a dense, permanent occupancy of the stent surface with Ac-heparin a direct cell contact to the metal surface is prevented. As in technical literature the emission of certain metal ions into the implant close tissue is discussed as one probable reason of restenosis, an anti-restenoic potency could be founded by one of the coating caused prevention of a direct metal contact.

On the other hand such a positive side effect is plausible, because on a passive, athrombogenenous stent surface with the absence of a platelet aggregation also the proliferative effects of the thereby released growth factors are to be missed. Thus an important, starting from the lumen side, stimulus of the neointimal proliferation is omitted.

Example 7

In vivo experiments of coronary stents coated with covalently bound Ac-heparin an a second suprajacent layer of PLGA 50/50

7.1 Hemocompatibility of the Used Matrix In Vitro

For evaluation of the hemocompatibility of PLGA 50/50 stainless steel stents were coated with the polymer and tested at the Intitute of Physiology of the RWTH Aachen by means of in vitro whole blood tests. The used established and standardized Chandler loop system is a dynamic closed tube system, which operates without the use of a pump. Within the scope of the hemocompatibility experiments whole blood, platelet factor 4 (PF4) and complement factor 5a (C5a) were determined (see FIG. 14-16). For reasons of comparison the uncoated stent was included.

Carrying Out of the Experiment:

Donor blood is taken up into 1.5 U/ml of heparin. The stents are introduced into PVC tubes (I.D. 3.5 mm, L=95 cm) and fixed via balloon catheter. The 4 tubes (K3-K6) and two empty tubes (L1, L2) are filled in each case with 7.5 ml isotonic sodium chloride solution and rotated for 15 minutes at 5 r/min at 37° C. in the Chandler loop. The completely emptied tubes are filled carefully with heparinated donor blood (7.5 ml) and rotated for 60 min at 5 r/min. Accordingly to the anticoagulants samples are taken in monovettes and sample jars respectively (PF4-CTAD, C5a-EDTA, BB-EDTA) and processed.

The determination of the platelet number shows no significant difference between the empty control tubes, the coated and non coated stents. The released PF4 is in case of the coated and non coated tubes at the same level. The determination of the activated complement factor 5 (C5a) shows in case of the coated stents a smaller activation as in case of the non coated stents.

7.2 Hemocompatibility of the Used Matrix In Vivo

The aim of the experiments was primarily to evaluate the influence of the PLGA-coating towards the stent induced vessel reaction. For the experiments 28 six to nine month old domestic porks were used. The stented areas were examined after one week (1WoFUP), one month (4WoFUP), six weeks (6WoFUP) and after three months (12WoFUP). The obtained data show an unexpected amazingly positive effect, which is due to the presence of PLGA 50/50 beyond doubt. Although the values of stenosis after three months hardly differ for the uncoated stent and for the coated stent, the reaction of the vessel wall towards the PLGA-coated stent is substantially smoother. After one week the stenosis value lies with 6% significantly below the value of the uncoated implants with 10.4%. The masking of the metal surface results after four weeks even with 10% (an increase of 33%) in a more than factor two lower stenosis rate than the uncoated stent, which reaches after this period of time its maximum value of 22.6% (an increase of 54%). The coated stent shows a maximum after six weeks with only 12.33%. After 12 weeks the values of both systems equal each other with approx. 11% (FIG. 16).

The data for the restenotic processes were determined via quantitative coronary angiography (QCA) and intravascular ultra sound examinations (IVUS).

Example 8

Experiments Concerning the Coating of Surfaces with Tacrolimus

Pre-Experiments with Toluidine Blue:

First pre-experiments are carried out with toluidine blue (Aldrich) since tacrolimus can be detected chemically quite difficult.

Chemicals:

| | |
|---|---|
| stainless steel tubes LVM 316: | 2.5 cm in length, 2 mm in diameter |
| polylactide: | Fluka, Lot. 398555/123500, HNo. 0409 |
| toluidine blue: | Aldrich, Lot. 19,816-1, HNo. 0430 |
| PBS-buffer pH 7.4: | 14.24 g $Na_2HPO_4$, 2.72 g $NaH_2PO_4$, 9 g NaCl |

Realization:

The stent is weighed out on the analytical balance and the weight is noted. In a small hydrolysis tube 0.5 g polylactide are dissolved in 2 ml of $CHCl_3$. Therefore, it is heated to 65° C. in the water bath. The solution is cooled down in the freezing compartment. Thereto are added 200 μg toluidine blue in 200 μl of $CHCl_3$. The stent is dipped into this solution. After a couple of minutes the stent is taken out of the solution with tweezers and moved within the fume hood until the solvent evaporates. Then the stent is dipped in for a second time. After air drying the stent is freeze dried for about 10 min. After the drying the stent is balanced again. The amount of the immobilized polylactide with toluidine blue is measured from the weight difference (sample 1).

This experiment is repeated another time with the same solution (sample 2).

For sample 3 the dipping solution (1.93 ml) which results from experiment 1 (sample 1) and experiment 2 (sample 2) is mixed with 0.825 mg toluidine blue in 0.825 ml of $CHCl_3$ and 250 mg polylactide. The polylactide is dissolved during heating. Then a stent is dipped into it two times as described above.

Results:

The untreated stents had a weight of 176.0 mg and 180.9 mg. After dipping into the polylactide solution the stents balanced 200.9 and 205.2 mg.

The dipping solution contains 500 mg polylactide and 200 μg toluidine blue. The bound amount of toluidine blue can be measured for the samples 1 and 2 from this ratio. In case of sample 3 2.755 ml solution contain 1 mg toluidine blue and 638.6 mg polylactide (initial weight–consumption sample 1+2; approx. 50 mg). Here two stents are given into one preparation to obtain higher absorptions. As the dipping solution was very viscous which yielded a very thick coating it was diluted from 2.625 ml with chloroform to 4 ml.

Concentrations in the Dipping Solution:

| sample | volume (ml) | c (polylactide mg/ml) | c (toluidine blue μg/ml) |
|---|---|---|---|
| 1 | 2.2 | 227.3 | 90.9 |
| 2 | 2.2 | 227.3 | 90.9 |
| 3 | 2.755 | 231.8 | 363.0 |
| 4 | 4.0 | 134.5 | 212.5 |

Weight of the Tubes and the Resultant Measured Coating:

| sample | net weight | total weight | PL & toluidine blue | Toluidine blue |
|---|---|---|---|---|
| 1 | 176.0 mg | 200.9 mg | 24.9 mg | 9.96 μg |
| 2 | 180.9 mg | 205.2 mg | 24.3 mg | 9.72 μg |
| 3 | 317.2 mg | 410.8 mg | 93.6 mg | 135.73 μg |
| 4 | 180.8 mg | 194.8 mg | 14.8 mg | 23.38 μg |

Example 9

Elution Behavior of the Coatings with Different Concentrations

As pre-experiment a UV-Vis spectra of a toluidine blue solution in ethanol is taken (c=0.1 mg/ml) and the absorption maximum is determined. The toluidine blue concentration in the solution is measured at an absorption maximum of 627 nm. Thereto a calibration curve is generated.

A stent is hung into a beaker with 25 ml of physiological sodium chloride solution in a phosphate buffer pH 7.4 (14.24 g $NaH_2PO_4$, 2.72 g $K_2HPO_4$ and 9 g NaCl) and stirred gently at room temperature. After 0.5, 1, 2, 3, 6, 24, 48 and 120 hours, each time a sample of 3 ml is taken, measured spectroscopically and given back into the preparation.

| time/h | abs. s1 | c (ng/ml) | abs. s2 | c (ng/ml) | abs. s3 | c (ng/ml) | abs. s4 | c (ng/ml) |
|---|---|---|---|---|---|---|---|---|
| 0 | 0.0002 | 0 | −0.0002 | 0 | 0.0036 | 0 | 0.0063 | 0 |
| 0.5 | −0.0011 | 0 | 0.0011 | 6.4 | 0.0095 | 29.2 | 0.0125 | 30.7 |
| 1 | 0.0003 | 0.5 | 0.0014 | 7.9 | 0.0164 | 63.3 | 0.0121 | 28.7 |
| 2 | 0.0007 | 2.5 | 0.0008 | 5.0 | 0.0256 | 108.9 | 0.0131 | 33.7 |
| 3 | −0.0004 | 0 | 0.0006 | 4.0 | 0.0294 | 127.7 | 0.0136 | 36.1 |
| 6 | 0.0013 | 5.4 | 0.0015 | 8.4 | 0.0333 | 147.0 | 0.0142 | 39.1 |
| 24 | 0.0017 | 7.4 | 0.0020 | 10.8 | 0.0527 | 246.0 | 0.0239 | 176 |
| 48/96 | 0.0024 | 10.9 | 0.0033 | 17.3 | 0.1096 | 524.8 | 0.0147 | 41.6 |
| 120 | 0.0017 | 7.4 | 0.0038 | 19.8 | 0.1110 | 531.7 | 0.0161 | 48.5 |

Absorption of the samples after different periods of time. For measuring of the concentration the cuvette difference (abs. at T=0) is subtracted from the measured value.

After 12 and 13 days respectively the experiment was terminated. On all of the stents after the expiration of the experiment a coating was still present. For determining the amounts of toluidine blue and polylactide respectively which were dissolved, the stents were rinsed with water and ethanol and then freeze dried during 1 h for balancing them afterwards.

| S. | final weight | initial weight | PL + Tb | diss. PL + Tb | diss. Tb. | rem. Tb. |
|---|---|---|---|---|---|---|
| 1 | 196.5 | 200.9 mg | 24.9 mg | 4.4 mg | 1.76 µg | 8.2 µg |
| 2 | 199.4 | 205.2 | 24.3 mg | 5.8 mg | 2.32 µg | 3.48 µg |
| 3 | 385.4 | 410.8 | 93.6 mg | 25.4 mg | 36.83 µg | 98.8 µg |
| 4 | 191.3 | 194.8 | 14.8 mg | 3.5 mg | 5.52 µg | 17.86 µg |

In case of concentrations of 90 µg toluidine blue per ml dipping solution the released amounts of toluidine blue are so low that the absorptions are at the detection limit of the spectrometer. In case of a concentration of 200 µg/ml the values are after a couple of hours in the measurable area. It is recommended for the measurement to place two samples into a beaker (elution jar) to yield higher absorptions. In case of the highest polylactide/toluidine blue concentration a saturation effect seems to appear. While the elution ratio in case of the thinner samples has an almost linear trajectory. On all of the stents the coating can still be detected after several days.

After approx. 2 weeks the bound toluidine blue dissolved in average from about ¼-⅕. Hence it results that the samples still would have eluted toluidine blue for approx. 8 to 10 weeks.

The dipping solution may not be too thick and should be cooled so that the chloroform cannot evaporate too fast during the extraction as else the thickness of the coating becomes too large and inhomogeneous. Here the polylactide concentration in sample 4 (134 mg/ml) seems to be sufficient, above all in case of higher concentrations the solution becomes extremely viscous and the polylactide is only very difficult to dissolve.

Example 10

Coating of the Stents Via the Spraying Method

The according to example 1 and example 2 pre-prepared not expanded stents are balanced and horizontally hung onto a thin metal bar (d=0.2 mm) which is stuck on the rotation axis of the rotation and feed equipment and rotates with 28 r/min. The stents are fixed in such way, that the interior of the stents does not touch the bar. At a feeding amplitude of 2.2 cm and a feeding velocity of 4 cm/s and a distance of 6 cm between stent and spray nozzle, the stent is sprayed with the respective spray solution. After the drying (about 15 minutes) at room temperature and proximately in the fume hood over night it is balanced again.

Example 11

Coating of the Stents with Pure Matrix

Preparation of the Spray Solution:

176 mg polylactide is balanced and replenished with chloroform to 20 g.

The stents are sprayed in each case with 3 ml of the spraying solution, balanced before and after the spraying and the yielding layer thickness is determined by measuring under the microscope 100-times magnified.

| stent No. | before coating | after coating | weight of coating | layer thickness |
|---|---|---|---|---|
| 1 | 0.0193 g | 0.0205 g | 1.2 mg | 10.4 µm |
| 2 | 0.0193 g | 0.0205 g | 1.2 mg | 10.4 µm |
| 3 | 0.0204 g | 0.0216 g | 1.2 mg | 10.4 µm |
| 4 | 0.0206 g | 0.0217 g | 1.1 mg | 10.4 µm |

Example 12

Coating of the Stents with Pure Active Agent

Preparation of the spray solution: 44 mg taxol are dissolved in 6 g chloroform.

The stents are balanced before and after the spraying.

| stent No. | before coating | after coating | weight of coating |
|---|---|---|---|
| 1 | 0.0194 g | 0.0197 g | 0.30 mg |

Example 13

Determination of the Elution Behaviour in PBS-Buffer

Each stent placed in a sufficiently small flask, 2 ml PBS-buffer is added, sealed with parafilm and incubated in the drying closet at 37° C. After expiry of the chosen time intervals in each case the supernatant is depipetted and its UV absorption at 306 nm is measured.

Example 14

Coating of the Hemocompatibly Equipped Stents with an Active Agent Loaded Matrix (FIG. 7)

Spray solution: Polylactide RG502/taxol - solution is replenished from 145.2 mg polylactide and 48.4 mg taxol to 22 g with chloroform.

| stent | spray solution | weight before (g) | weight after (g) | weight of coating | weight of active agent | active agent µg/mm² | layer thickness |
|---|---|---|---|---|---|---|---|
| 1 | 0.8 ml | 0.02180 | 0.02215 | 0.35 mg | 146 µg | 1.97 | 7.9 µm |
| 2 | 0.8 ml | 0.02105 | 0.02142 | 0.37 mg | 154 µg | 2.08 | 6.7 µm |
| 3 | 0.8 ml | 0.02247 | 0.02285 | 0.38 mg | 158 µg | 2.14 | 9.8 µm |
| 4 | 0.8 ml | 0.02395 | 0.02432 | 0.37 mg | 154 µg | 2.08 | 11.0 µm |
| 5 | 0.8 ml | 0.02247 | 0.02286 | 0.39 mg | 163 µg | 2.20 | 9.1 µm |
| 6 | 0.8 ml | 0.02442 | 0.02482 | 0.40 mg | 167 µg | 2.26 | 12.2 µm |

Example 15

Coating of the Stents with an Active Agent Loaded Matrix and an Active Agent as Topcoat (FIG. 8)

Basis coat: 19.8 mg polylactide and 6.6. mg taxol are replenished with chloroform to 3 g.

Topcoat: 8.8 mg taxol are replenished with chloroform to 2 g.

| stent | spray solution | weight before (g) | weight after (g) | weight of coating | weight of active agent | active agent µg/mm² | layer thickness |
|---|---|---|---|---|---|---|---|
| 1 | 0.85 ml | 0.0235 | 0.0238 | 0.30 mg | 131 µg | 1.56 | 9.7 µm |
| 2 | 0.85 ml | 0.0260 | 0.0264 | 0.40 mg | 175 µg | 2.09 | 10.1 µm |

Example 16

Coating of the Stents with a Polylactide which Contains a Hydrophilic Active Agent and with an Active Agent Free Matrix as Topcoat (FIG. 9)

Spray Solutions:

Basis coating: 22 mg polylactide and 22 mg hydrophilic active agent are balanced and replenished with chloroform to 5 g.

Topcoat: 22 mg polylactide and 22 mg polystyrene are balanced and replenished with chloroform to 5 g.

| spray solution | before coating | after coating | weight of coating | weight of active agent |
|---|---|---|---|---|
| 0.85 ml | 0.0135 g | 0.0143 g | 0.8 mg | 200 µg |

What is claimed is:

1. A metal stent, wherein the surface of the stent is coated directly and covalently with a hemocompatible layer, comprising at least one oligosaccharide and/or polysaccharide according to formulas (Ia) or (Ib):

Formula (Ia)

Formula (Ib)

wherein n is an integer between 4 and 1050,

Y and Z, independently of each other, represent the groups —CHO, —COCH$_3$, —COC$_2$H$_5$, —COC$_3$H$_7$, —COC$_4$H$_9$, —COC$_5$H$_{11}$, —COCH(CH$_3$)$_2$, —COCH$_2$CH(CH$_3$)$_2$, —COCH(CH$_3$)C$_2$H$_5$, —COC(CH$_3$)$_3$, —CH$_2$COO—, —C$_2$H$_4$COO—, —C$_3$H$_6$COO—, —C$_4$H$_8$COO—, and salts of said compounds.

2. The stent according to claim 1, further comprising at least one biostable and/or biodegradable layer on the hemocompatible layer, and at least one additional hemocompatible layer on the biostable and/or biodegradable layer.

3. The stent according to claim 1, wherein the hemocompatible layer is coated completely or incompletely with at least one, superjacent biostable and/or biodegradable layer.

4. The stent according to claim 2, wherein at least one active agent layer is present between the biostable and/or biodegradable layer and the hemocompatible layer covalently bonded to the stent, and wherein the active agent layer comprises at least one antiproliferative, antiinflammatory and/or antithrombotic active agent.

5. The stent according to claim 1, wherein at least one antiproliferative, antiinflammatory and/or antithrombotic active agent is bound covalently and/or adhesively in and/or on the hemocompatible layer.

6. The stent according to claim 5, wherein the at least one antiproliferative, antiinflammatory and/or antithrombotic active agent is selected from the group consisting of sirolimus (rapamycin), everolimus, pimecrolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxyoxycyclophosphamide, estramustine, melphalan, ifosfamide, tropfosfamide, chlorambucil, bendamustine, dacarbazine, busulfan, procarbazine, treosulfan, thymosin α-1, tremozolomide, thiotepa, tialin (2-methylthiazolidine-2,4-dicarboxylic acid), tialin-Na (sodium salt of tialin), aunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegasparase, anastrozole, exemestane, letrozole, formestane, aminoglutethemide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, muparfostat, melanocyte stimulating hormon (α-MSH), activated protein C, IL1-β inhibitor, fumaric acid and its esters, dermicidin, calcipotriol, tacalcitol, lapachol, β-lapachone, podophyllotoxin, betulin, podophyllic acid 2-ethylhydrazide, molgramostim (rhuGM-CSF), peginterferon α-2b, lanograstim (r-HuG-CSF), filgrastim, dacarbazine, letrozol, goserelin, trastuzumab, exemestan, basiliximab, daclizumab, selectin (cytokine antagonist), CETP inhibitor, cadherines, cytokinin inhibitors, COX-2 inhibitor, NFkB, angiopeptin, (1-cyclopropyl-6-fluoro-4-oxo-7-(piperazin-1-yl)-quinoline-3-carboxylic acid), fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopolectin, colchicine, NO donors, tamoxifen, staurosporine, β-estradiol, α-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, paclitaxel, baccatin, synthetically and from native sources obtained macrocyclic oligomers of carbon suboxide (MCS), mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, f3-sitosterin, ademetionine, myrtecaine, polidocanol, nonivamide, levomenthol, benzocaine, aescin, ellipticine, N-(Pyridin-4-yl)-[1-(4-chlorobenzyl)-indol-3-yl]-glyoxyl Amide, ((S)-6,7-Dihydro-1,2,3,10-tetramethoxy-7-(methylamino)benzo[α]heptalen-9 (5H)-on), cytochalasin A-E, indanocine, nocadazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plaminogen activator inhibitor-1, plasminogen activator inhibitor-2, antisense oligonucleotides, VEGF inhibitors, IGF-1, active agents from the group of antibiotics, cefazolin, cefaclor, cefotixin, tobramycin, gentamycin, penicillins, oxacillin, sulfonamides, metronidazol, antithrombotics, aspirin, abciximab, synthetic antithrombin, bivalirudin, warfarin sodium, enoxoparin, tissue plasminogen activator, GpIIb/IIIa platelet membrane receptor, factor Xa inhibitor antibody, heparin, hirudin, r-hirudin, PPACK, protamin, prourokinase, streptokinase, urokinase, vasodilators, trapidil, nitroprussides, PDGF antagonists, ACE inhibitors, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, NF-kB or Bc1-xL antisense oligonucleotides, halofuginone, nifedipine, tocopherol, tranirast, molsidomine, tea polyphenols, epicatechin gallate, epigallocatechin gallate, Boswellic acids, leflunomide, anakinra, etanercept, sulfasalazine, etoposide, dicloxacillin, tetracycline, triamcinolone, procainimid, retinoic acid, quinidine, disopyrimide, flecamide, propafenone, sotolol, amidorone, natural and synthetically obtained steroids, inotodiol, maquiroside A, mansonine, hydrocortisone, betamethasone, dexamethasone, non-steroidal substances (NSAIDS), ibuprofen, indomethacin, naproxen, phenylbutazone and other antiviral agents, ganciclovir and zidovudine, antimycotics, flucytosine, griseofulvin, ketoconazole, miconazole, nystatin, terbinafine, antiprozoal agents, mefloquine, quinine, natural terpenoids, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-α-senecioyloxychaparrin, taxamairin A and B, regenilol, triptolide, cymarin, apocymarin, aristolochic acid, anopterin, hydroxyanopterin, anemonin, protoanemonin, cheliburin chloride, cictoxin, sinococuline, bombrestatin A and B, cudraisoflavone A, curcumin, dihydronitidine, nitidine chloride, 12-β-hydroxypregnadien-3,20-dione, bilobol, ginkgol, ginkgolic acid, helenalin, indicine, indicine-N-oxide, lasiocarpine, glycoside 1a, podophyllotoxin, justicidin A and B, larreatin, malloterin, mallotochromanol, isobutyrylmallotochromanol, marchantin A, maytansine, lycoridicin, margetine, pancratistatin, liriodenine, bisparthenolidine, aristolactam-AII, periplocoside A, ghalakinoside, deoxypsorospermin, psycorubin, ricin A, sanguinarine, manwu wheat acid, methylsorbifolin, spatheliachromen, stizophyllin, strebloside, akagerine, dihydrousambaraensine, hydroxyusambarine, strychnopentamine, strychnophylline, usambarine, usambarensine, (5,6-dihydro-9,10-dimethoxybenzo[g]-1,3-benzodioxolo[5,6-a]quinolizinium), oxoushinsunine, daphnoretin, lariciresinol, methoxylariciresinol, syringaresinol, umbelliferon, afromoson, acetylvismione B, desacetylvismione A, vismione A, and vismione B.

7. The stent according to claim 6, wherein the at least one antiproliferative, antiinflammatory and/or antithrombotic active agent is selected from the group consisting of tacrolimus, pimecrolimus, muparfostat, thymosin α-1, PETN, baccatine, docetaxel, colchicin, paclitaxel, trapidil, α- and β-estradiol, dermicidin, tialin-sodium, simvastatin, macrocyclic suboxide (MCS), sirolimus, tyrphostine, N-(Pyridin-4-yl)-[1-(4-chlorobenzyl)-indol-3-yl]-glyoxyl Amide, fumaric acid and its esters, activated protein C (aPC), interleukin 1β inhibitors and melanocyte stimulating hormon (α-MSH) as well as mixtures of these active agents.

8. The stent according to claim 1, further comprising a polymer deposited in amounts between 0.01 mg to 3 mg/layer.

9. The stent according to claim 4, wherein the antiproliferative, antiinflammatory and/or antithrombotic active agent is comprised in a pharmaceutically active concentration of 0.001-10 mg per cm² stent surface.

10. A metallic stent, wherein the surface of the stent is coated with a hemocompatible layer comprising at least one oligosaccharide and/or polysaccharide according to formulas (Ia) or (Ib) and at least one interjacent biostable layer, wherein the interjacent biostable layer is covalently bonded to the stent and wherein the hemocompatible layer is covalently bonded to the interjacent biostable layer

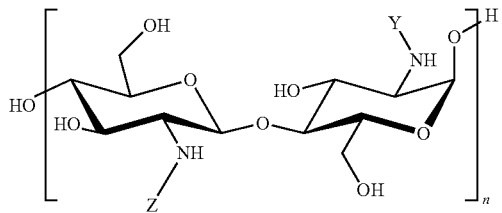

Formula (Ia)

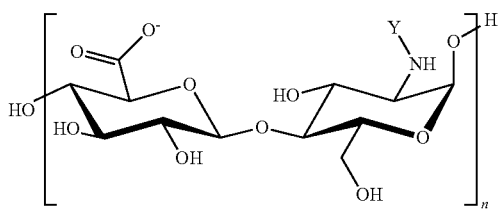

Formula (Ib)

wherein
n is an integer between 4 and 1050,
Y and Z, independently of each other, represent the groups
—CHO, —COCH$_3$, —COC$_2$H$_5$, —COC$_3$H$_7$, —COC$_4$H$_9$, —COC$_5$H$_{11}$, —COCH(CH$_3$)$_2$, —COCH$_2$CH(CH$_3$)$_2$, —COCH(CH$_3$)C$_2$H$_5$, —COC(CH$_3$)$_3$, —CH$_2$COO$^-$, —C$_2$H$_4$COO$^-$, —C$_3$H$_6$COO$^-$, —C$_4$H$_8$COO$^-$, and salts of said compounds.

11. The stent according to claim 10, wherein at least one antiproliferative, antiinflammatory and/or antithrombotic active agent is bound covalently and/or adhesively in and/or on the hemocompatible layer.

12. The stent according to claim 11, wherein the at least one antiproliferative, antiinflammatory and/or antithrombotic active agent is chosen from the group consisting of tacrolimus, pimecrolimus, muparfostat, thymosin α-1, PETN, baccatine, docetaxel, colchicin, paclitaxel, trapidil, α- and β-estradiol, dermicidin, tialin-sodium, simvastatin, macrocyclic suboxide (MCS), sirolimus, tyrphostine, N-(Pyridin-4-yl)-[1-(4-chlorobenzyl)-indol-3-yl]-glyoxyl Amide, fumaric acid and its esters, activated protein C (aPC), interleukin 1β inhibitors and melanocyte stimulating hormone (α-MSH) as well as mixtures of these active agents.

13. The stent according to claim 5, wherein the antiproliferative, anti-inflammatory and/or antithrombotic active agent is comprised in a pharmaceutically active concentration of 0.001-10 mg per cm² stent surface.

* * * * *